US012642941B2

(12) United States Patent
Boyum et al.

(10) Patent No.: US 12,642,941 B2
(45) Date of Patent: Jun. 2, 2026

(54) SECURING A CATHETER DEVICE

(71) Applicant: INTERRAD Medical, Inc., Plymouth, MN (US)

(72) Inventors: Erik Andrew Boyum, Shoreview, MN (US); Jeffrey D. Killion, Orono, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 974 days.

(21) Appl. No.: 17/856,517

(22) Filed: Jul. 1, 2022

(65) Prior Publication Data

US 2023/0021353 A1     Jan. 26, 2023

Related U.S. Application Data

(60) Provisional application No. 63/225,634, filed on Jul. 26, 2021.

(51) Int. Cl.
*A61M 25/02*      (2006.01)
*A61B 17/34*      (2006.01)
(Continued)

(52) U.S. Cl.
CPC ......... *A61M 25/02* (2013.01); *A61B 17/3415* (2013.01); *A61B 17/3421* (2013.01);
(Continued)

(58) Field of Classification Search
CPC .................. A61M 25/02; A61M 25/04; A61M 2005/1586; A61M 2025/024; A61M 2025/028; A61M 2025/0286; A61M 2025/0233; A61M 2210/04; A61M 2039/0223; A61M 2039/0258; A61M 2039/0261; A61M 39/0208; A61M 2005/1585; A61M 2005/1587; A61M 2025/0246; A61M 39/0247; A61B 17/3415; A61B 17/3421; A61B 2017/3488; A61B 2017/3492
See application file for complete search history.

(56) References Cited

U.S. PATENT DOCUMENTS 3,039,468 A     6/1962   Price
3,308,819 A     3/1967   Arp
(Continued)

FOREIGN PATENT DOCUMENTS

EP          2614851        7/2013
WO     WO 1991015254     10/1991
(Continued)

OTHER PUBLICATIONS

International Search Report and Written Opinion in International Appln. No. PCT/US2022/035993, mailed on Nov. 25, 2022, 13 pages.
(Continued)

*Primary Examiner* — William R Carpenter
*Assistant Examiner* — Robert F Allen
(74) *Attorney, Agent, or Firm* — Fish & Richardson P.C.

(57)          ABSTRACT

Some embodiments of a medical system include a catheter device, such as an intravenous cannula device, having an external anchor device and a subcutaneous anchor device to secure a distally extending cannula of the device in a selected position relative to a skin penetration point.

12 Claims, 10 Drawing Sheets

(51) Int. Cl.

| | | |
|---|---|---|
| *A61M 5/158* | (2006.01) | |
| *A61M 25/04* | (2006.01) | |
| *A61M 39/02* | (2006.01) | |

(52) U.S. Cl.

CPC ................. *A61B 2017/3484* (2013.01); *A61B 2017/3488* (2013.01); *A61B 2017/3492* (2013.01); *A61M 2005/1585* (2013.01); *A61M 2005/1586* (2013.01); *A61M 2005/1587* (2013.01); *A61M 2025/024* (2013.01); *A61M 2025/0246* (2013.01); *A61M 2025/028* (2013.01); *A61M 2025/0286* (2013.01); *A61M 2025/0293* (2013.01); *A61M 25/04* (2013.01); *A61M 39/0208* (2013.01); *A61M 39/0247* (2013.01); *A61M 2039/0258* (2013.01); *A61M 2039/0261* (2013.01); *A61M 2210/04* (2013.01)

(56) References Cited

U.S. PATENT DOCUMENTS

| | | | | |
|---|---|---|---|---|
| 3,765,032 | A | | 10/1973 | Palma |
| 3,856,009 | A | | 12/1974 | Winnie |
| 3,896,527 | A | | 7/1975 | Miller |
| 3,938,529 | A | | 2/1976 | Gibbons |
| 4,043,346 | A | | 8/1977 | Mobley |
| 4,114,618 | A | | 9/1978 | Vargas |
| 4,164,943 | A | | 8/1979 | Hill |
| 4,248,224 | A | | 2/1981 | Jones |
| 4,309,994 | A | | 1/1982 | Grunwald |
| 4,397,647 | A | | 8/1983 | Gordon |
| 4,474,569 | A | | 10/1984 | Newkirk |
| 4,498,902 | A | * | 2/1985 | Ash .................. A61M 25/0668 |
| | | | | 600/585 |
| 4,543,100 | A | * | 9/1985 | Brodsky .............. A61M 25/02 |
| | | | | 128/DIG. 26 |
| 4,569,344 | A | | 2/1986 | Palmer |
| 4,592,356 | A | | 6/1986 | Gutierrez |
| 4,645,492 | A | | 2/1987 | Weeks |
| 4,665,906 | A | | 5/1987 | Jervis |
| 4,799,495 | A | | 1/1989 | Hawkins |
| 4,804,359 | A | | 2/1989 | Grunwald |
| 4,813,930 | A | | 3/1989 | Elliott |
| 4,936,823 | A | | 6/1990 | Colvin |
| 4,986,810 | A | | 1/1991 | Semrad |
| 5,041,085 | A | | 8/1991 | Osborne |
| 5,067,957 | A | | 11/1991 | Jervis |
| 5,122,122 | A | | 6/1992 | Allgood |
| 5,190,546 | A | | 3/1993 | Jervis |
| 5,256,146 | A | | 10/1993 | Ensminger |
| 5,267,960 | A | | 12/1993 | Hayman |
| 5,279,564 | A | * | 1/1994 | Taylor .................... A61B 17/34 |
| | | | | 606/198 |
| 5,312,337 | A | | 5/1994 | Flaherty |
| 5,344,439 | A | | 9/1994 | Otten |
| 5,368,017 | A | | 11/1994 | Sorenson |
| 5,378,239 | A | | 1/1995 | Termin |
| 5,391,159 | A | | 2/1995 | Hirsh et al. |
| 5,456,671 | A | | 10/1995 | Bierman |
| 5,496,277 | A | | 3/1996 | Termin |
| 5,578,013 | A | | 11/1996 | Bierman |
| 5,597,378 | A | | 1/1997 | Jervis |
| 5,599,311 | A | | 2/1997 | Raulerson |
| 5,653,718 | A | | 8/1997 | Yoon |
| 5,681,288 | A | | 10/1997 | Schlitt |
| 5,688,247 | A | | 11/1997 | Haindl |
| 5,702,371 | A | | 12/1997 | Bierman |
| 5,707,362 | A | | 1/1998 | Yoon |
| 5,722,959 | A | | 3/1998 | Bierman |
| 5,728,133 | A | | 3/1998 | Kontos |
| 5,741,234 | A | | 4/1998 | Aboul-Hosn |
| 5,746,720 | A | | 5/1998 | Stouder, Jr. |
| 5,755,697 | A | | 5/1998 | Jones |
| 5,769,821 | A | | 6/1998 | Abrahamson |

| | | | | |
|---|---|---|---|---|
| 5,800,390 | A | * | 9/1998 | Hayakawa ........ A61M 39/0208 |
| | | | | 604/93.01 |
| 5,800,402 | A | | 9/1998 | Bierman |
| 5,810,781 | A | | 9/1998 | Bierman |
| 5,814,065 | A | | 9/1998 | Diaz |
| 5,827,230 | A | | 10/1998 | Bierman |
| 5,833,664 | A | | 11/1998 | Seare, Jr. |
| 5,833,667 | A | | 11/1998 | Bierman |
| 5,857,999 | A | * | 1/1999 | Quick ................... A61M 25/04 |
| | | | | 604/174 |
| 5,921,965 | A | | 7/1999 | Blei |
| 5,928,266 | A | | 7/1999 | Kontos |
| 5,931,730 | A | * | 8/1999 | Bernhardt ............ A22B 5/0082 |
| | | | | 452/65 |
| 5,944,732 | A | | 8/1999 | Raulerson |
| 5,947,931 | A | | 9/1999 | Bierman |
| 5,971,960 | A | | 10/1999 | Flom |
| 5,984,896 | A | | 11/1999 | Boyd |
| 5,989,265 | A | | 11/1999 | Bouquet De La Joliniere |
| 6,213,979 | B1 | | 4/2001 | Bierman |
| 6,290,676 | B1 | | 9/2001 | Bierman |
| 6,413,240 | B1 | | 7/2002 | Bierman |
| 6,447,485 | B2 | | 9/2002 | Bierman |
| 6,540,693 | B2 | | 4/2003 | Burbank |
| 6,572,588 | B1 | | 6/2003 | Bierman |
| 6,582,388 | B1 | | 6/2003 | Coleman |
| 6,582,403 | B1 | | 6/2003 | Bierman |
| 6,663,600 | B2 | | 12/2003 | Bierman |
| 6,679,851 | B2 | | 1/2004 | Burbank |
| 6,695,861 | B1 | | 2/2004 | Rosenberg |
| 6,770,055 | B2 | | 8/2004 | Bierman |
| 6,896,665 | B2 | | 5/2005 | Picha |
| 6,958,044 | B2 | | 10/2005 | Burbank |
| 7,056,286 | B2 | | 6/2006 | Ravenscroft |
| 7,695,492 | B1 | | 4/2010 | Ashby et al. |
| 8,825,129 | B2 | * | 9/2014 | Garcia ..................... A61N 1/05 |
| | | | | 604/512 |
| 8,932,263 | B2 | | 1/2015 | Rosenberg |
| 9,782,567 | B2 | | 10/2017 | Rosenberg |
| 10,532,188 | B2 | | 1/2020 | Rosenberg et al. |
| 2002/0068898 | A1 | | 6/2002 | McGucklin, Jr. |
| 2002/0068899 | A1 | | 6/2002 | McGucklin, Jr. |
| 2002/0120250 | A1 | | 8/2002 | Altman |
| 2002/0165489 | A1 | | 11/2002 | McGucklin, Jr. |
| 2004/0143237 | A1 | * | 7/2004 | Hart ...................... A61M 25/04 |
| | | | | 604/506 |
| 2005/0171588 | A1 | | 8/2005 | Wahlstrom |
| 2005/0187578 | A1 | | 8/2005 | Rosenberg |
| 2005/0256458 | A1 | | 11/2005 | Howard |
| 2005/0256459 | A1 | | 11/2005 | Howard |
| 2006/0079845 | A1 | | 4/2006 | Howard |
| 2006/0129134 | A1 | | 6/2006 | Kerr |
| 2007/0021685 | A1 | | 1/2007 | Oepen |
| 2007/0106330 | A1 | | 5/2007 | Rosenberg |
| 2007/0225651 | A1 | | 9/2007 | Rosenberg |
| 2007/0232997 | A1 | | 10/2007 | Glenn |
| 2008/0275401 | A1 | | 11/2008 | Sage |
| 2008/0287878 | A1 | * | 11/2008 | Tanaka ................... A61M 25/04 |
| | | | | 604/174 |
| 2008/0312599 | A1 | * | 12/2008 | Rosenberg ............ A61M 25/04 |
| | | | | 604/175 |
| 2009/0326470 | A1 | | 12/2009 | Rosenberg |
| 2010/0057010 | A1 | * | 3/2010 | Goransson ......... A61B 17/3417 |
| | | | | 604/164.04 |
| 2010/0081990 | A1 | * | 4/2010 | Swisher ............. A61B 17/3421 |
| | | | | 604/101.05 |
| 2011/0009828 | A1 | * | 1/2011 | Prechtel .............. A61J 15/0065 |
| | | | | 604/175 |
| 2011/0098681 | A1 | * | 4/2011 | Djurivic ............. A61B 17/0057 |
| | | | | 606/195 |
| 2011/0112364 | A1 | * | 5/2011 | Rone ................... A61B 17/3474 |
| | | | | 600/114 |
| 2011/0112508 | A1 | * | 5/2011 | Panzirer ............ A61M 25/0606 |
| | | | | 604/246 |
| 2012/0010563 | A1 | * | 1/2012 | Ravikumar ....... A61M 25/0662 |
| | | | | 604/171 |
| 2012/0180787 | A1 | * | 7/2012 | Bosel ................ A61M 16/0459 |
| | | | | 128/200.26 |

(56) References Cited

U.S. PATENT DOCUMENTS

| | | | |
|---|---|---|---|
| 2012/0197204 A1* | 8/2012 | Helm, Jr. | A61M 25/0631 |
| | | | 604/176 |
| 2013/0218127 A1* | 8/2013 | Rosenberg | A61M 25/02 |
| | | | 604/164.04 |
| 2015/0157845 A1* | 6/2015 | Bayly | A61M 39/10 |
| | | | 29/428 |
| 2016/0038650 A1* | 2/2016 | Griffith | A61M 25/02 |
| | | | 604/332 |
| 2016/0151608 A1 | 6/2016 | Aklog et al. | |
| 2018/0169387 A1 | 6/2018 | Rosenberg et al. | |
| 2020/0114123 A1 | 4/2020 | Rosenberg et al. | |
| 2020/0397667 A1* | 12/2020 | Zarnegar | A61J 15/0026 |
| 2021/0346053 A1* | 11/2021 | Tokarz | A61B 17/3421 |
| 2021/0346054 A1* | 11/2021 | Desjardin | A61B 17/3421 |

FOREIGN PATENT DOCUMENTS

| | | |
|---|---|---|
| WO | WO 2001021242 | 3/2001 |
| WO | WO 2004026152 | 4/2004 |
| WO | WO 2005039419 | 5/2005 |
| WO | WO 2005102438 | 11/2005 |
| WO | WO 2007093957 | 8/2007 |
| WO | WO 2010059714 | 5/2010 |
| WO | WO 2012007944 | 1/2012 |

OTHER PUBLICATIONS

Implant Manual, "Interstim Therapy: Model 3093 Lead and Model 3889 Lead," Medtronic, Inc., Minneapolis, MN, 2010, 38 pages.
Johnson & Johnson [online], "The EndoANCHOR Comparative Summary," retrieved on Sep. 13, 2005, 2 pages.
Johnson & Johnson [online], "The EndoANCHOR Features and Benefits," retrieved on Sep. 13, 2005, 2 pages.
Johnson & Johnson [online], "The EndoANCHOR Firing Sequences," retrieved on Sep. 13, 2005, 2 pages.
Web Page Printout of Statlock Device, publicly available before Feb. 17, 2012, 2 pages.
International Preliminary Report on Patentability in International Appln. No. PCT/US2022/035993, mailed on Feb. 8, 2024, 9 pages.

* cited by examiner

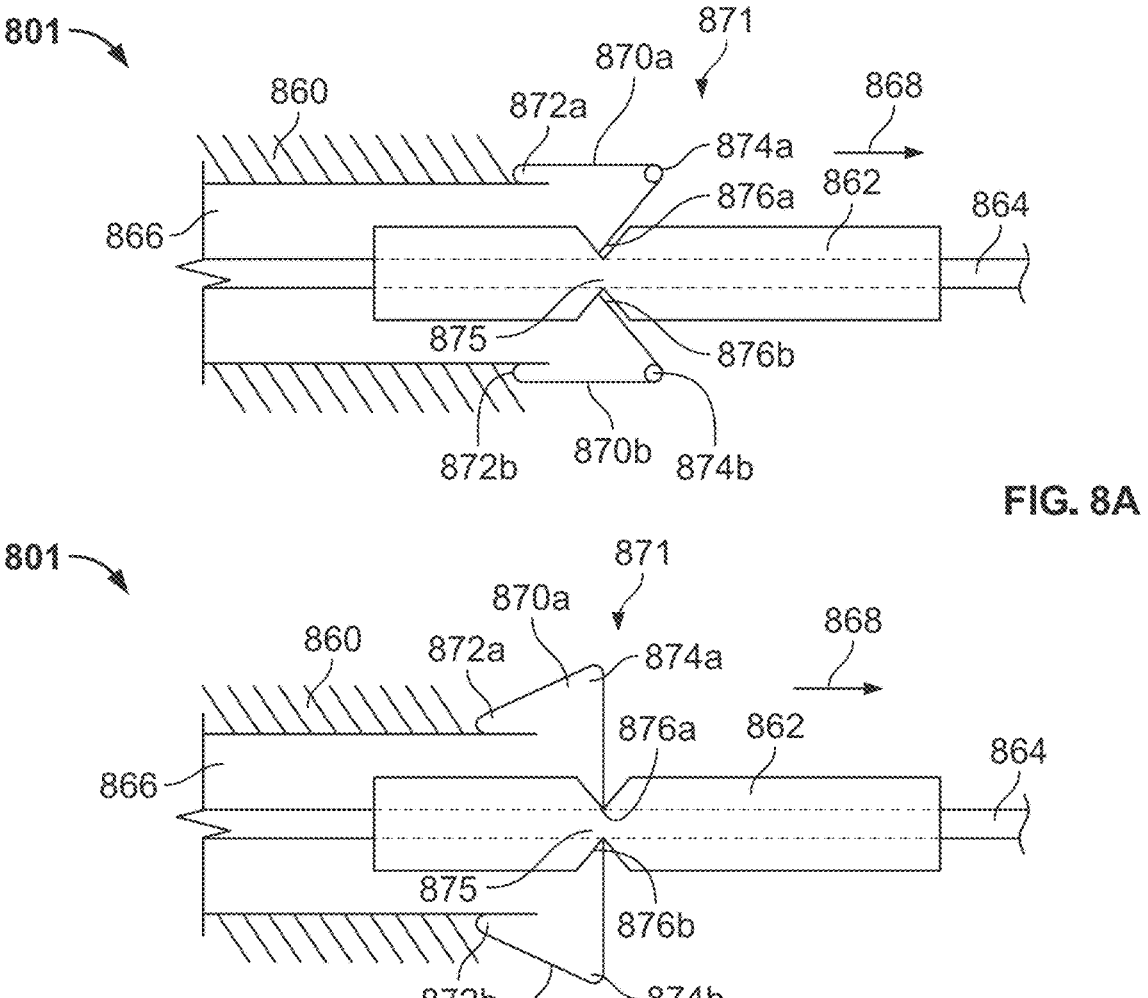
FIG. 8A
FIG. 8B
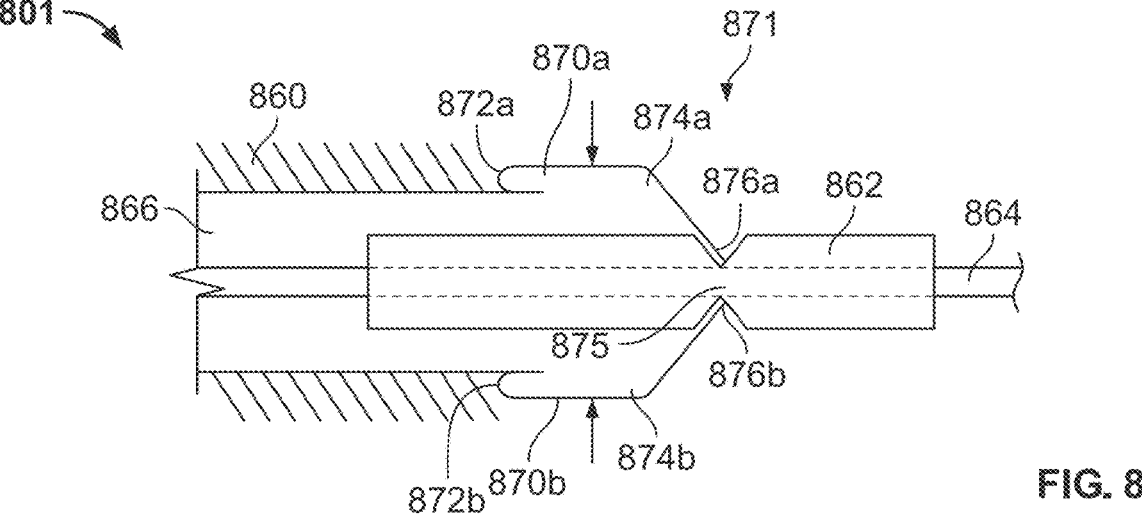
FIG. 8C

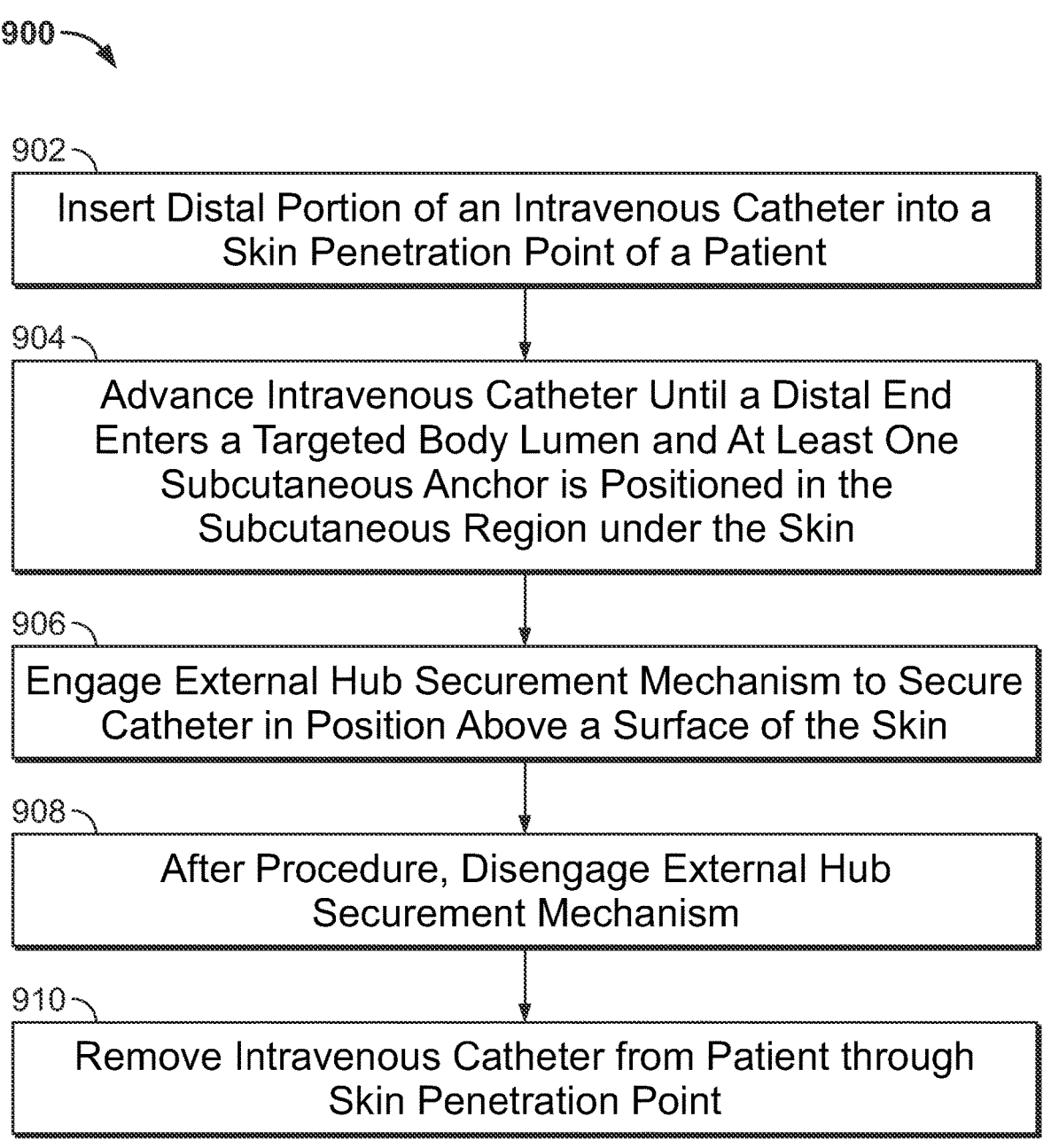

900

902
Insert Distal Portion of an Intravenous Catheter into a Skin Penetration Point of a Patient 904
Advance Intravenous Catheter Until a Distal End Enters a Targeted Body Lumen and At Least One Subcutaneous Anchor is Positioned in the Subcutaneous Region under the Skin 906
Engage External Hub Securement Mechanism to Secure Catheter in Position Above a Surface of the Skin 908
After Procedure, Disengage External Hub Securement Mechanism 910
Remove Intravenous Catheter from Patient through Skin Penetration Point

FIG. 9

SECURING A CATHETER DEVICE

TECHNICAL FIELD

This document relates to a medical device configured to anchor a catheter line (such as an intravenous catheter) to a skin penetration point, for example, using an integrated anchor mechanism.

BACKGROUND

Some medical devices are configured to provide intravenous therapy in which an infusion of a fluid is administered through an intravenous cannula. The intravenous cannula normally includes a distal tip region that is configured to insert through a skin opening and into a selected body vessel (e.g., a vein a patient's arm or leg) while a proximal hub remains external to skin opening for connection with a separate medicinal fluid line. This type of intravenous infusion therapy provides a direct route to the bloodstream which allows for hydration, administration of blood or blood products and administration of medications. Medications that are administered intravenously can achieve therapeutic effects more rapidly and, in some cases, using a lower dose.

Typical intravenous cannulas may extend for several inches in length and normally include a fluid lumen that extends to a distal port and the tip of the cannula. In some version, the intravenous cannula may include a hub structure, which can include large, flat "wings" or "tabs" that remain external to the skin and are equipped to adhere to the outer surface of the patient's skin. In other circumstances, the intravenous cannula may be secured to the skin penetration site using adhesive tape that is wrapped around an outer circumferential surface region of the intravenous cannula and around an adjacent portion of the patient's arm or leg. Alternatively, the intravenous cannula included a subcutaneous anchor system formed as a unitary structure with the side wall of the intravenous cannula.

SUMMARY

Some embodiments of a medical system include both an exterior anchor device and a subcutaneous anchor device that work in conjunction with one another at a location proximate to a skin penetration point of an catheter cannula (such as the cannula of an intravenous catheter) so as to secure the cannula in a position relative to the penetration point. In some circumstances, the exterior anchor device is movable relative to the hub of the catheter cannula so that it can be adjustably and selectively positioned against an exterior surface of the skin proximate to the skin penetration point while the subcutaneous anchor device resides in a subcutaneous region along an underside of the skin. Optionally, the exterior anchor device can be integrated with a hub of the catheter (such as an intravenous cannula hub of an intravenous catheter) to form a hub securement mechanism that can be moved relative to the hub and locked into a selected position relative to the hub to hinder forward motion of the catheter cannula in a distal direction (e.g., in a direction toward the distal tip of the cannula). In some circumstances, the exterior anchor device can be integrally or removably attached to the side wall of the catheter cannula. Optionally, the exterior anchor device reduces the likelihood of distal migration of the catheter cannula further through the skin penetration point while simultaneously the subcutaneous anchor device reduces the likelihood of proximal migration of the catheter cannula out of the skin penetration point. Accordingly, in some of the embodiments described herein, both an exterior anchor device and a subcutaneous anchor can be implemented together with an catheter cannula to contemporaneously anchor the catheter cannula on both the exterior side of the skin and the underside of the skin, thereby hindering migration of the catheter cannula during use and reducing the likelihood of infection at the skin penetration point.

Particular embodiments described herein include a catheter device for securing at a targeted site. The catheter device may include a flexible catheter configured to extend through a skin penetration point into a blood vessel, and the flexible catheter can have a distal opening at a distal end. The catheter device may optionally include a tissue anchor device positioned on an exterior surface of the flexible catheter device. Further, the catheter device may include an external anchor device positionable along a longitudinal axis of the exterior surface of the flexible catheter device. The tissue anchor device can be configured to anchor under a skin layer proximate to the skin penetration point while the external anchor device is positioned proximal of the tissue anchor device and adjacent to an exterior skin surface proximate to the skin penetration point.

Further embodiments include a medical system for anchoring an intravenous cannula device with respect to a skin surface. The system may include at least a proximal hub, an intravenous cannula, and an external anchor device. The proximal hub may include a hub body having a proximal end, a distal end, and a longitudinal axis extending from the proximal end to the distal end. The intravenous cannula may include a flexible catheter having an exterior circumferential surface configured to extend through a skin penetration point into a target body vessel, and the flexible catheter may extend distally of the proximal hub to a distal opening at a distal end. The intravenous cannula may optionally include a tissue anchor device positioned on an exterior surface of the flexible catheter between the distal opening and the distal end of the hub. The external anchor device may be configured to at least partially surround the flexible catheter, and the external anchor device may define a stopper element with a lateral dimension greater than the exterior circumferential surface of the flexible catheter. Optionally, the tissue anchor device is configured to anchor under a skin layer of the patient and the external anchor device is configured to be positioned distal of the hub body and proximal of the tissue anchor device such that the external anchor device is adjacent to the skin surface.

Other embodiments also include a medical system for anchoring an intravenous cannula device with respect to a skin surface. The system may include a proximal hub comprising a hub body having a proximal end, a distal end, and a longitudinal axis extending from the proximal end to the distal end. The system may also include an external anchor device coupled to the hub body. The external anchor device can be configured to at least partially surround the flexible catheter, and the external anchor device may optionally include an advancement mechanism and a contact portion. The contact portion may have a lateral dimension greater than a diameter of a skin opening dimension defined by a flexible catheter, and the external anchor device can be configured to be advanced in the direction of the longitudinal axis of the hub body along the flexible catheter. The system may further include an intravenous cannula, which comprises the flexible catheter configured to extend through a skin penetration point and define the skin opening dimension. The flexible catheter may extend distally of the proximal hub to a distal opening at a distal end. The intravenous cannula may also include a tissue anchor device positioned on an exterior surface of the flexible catheter between the distal opening and the distal end of the hub. The tissue anchor device can be configured to anchor under a skin layer of the patient and the external anchor device can configured to be positioned distal of the hub body and proximal of the tissue anchor device such that the external anchor device is adjacent to the skin surface.

Some embodiments described herein include a method for securing an intravenous cannula in a selected position. The method can include inserting a distal portion of an intravenous cannula into a skin penetration point of a skin surface. Also, the method may include advancing the intravenous cannula until a distal end enters a target body lumen and, and optionally, at least one subcutaneous anchor is positioned in a subcutaneous region under the skin surface. The method may further include engaging an external anchor to secure the intravenous cannula in a position above and adjacent to the skin surface. The method can include performing a medical procedure using the intravenous cannula. Optionally, the method may include, after the medical procedure is performed, disengaging the external anchor. The method can also include removing the intravenous cannula through the skin penetration point.

Further embodiments described herein include a method for securing an intravenous cannula in a selected position. The method may include inserting a distal end of an intravenous cannula into a skin penetration point such that a subcutaneous anchor of the intravenous cannula is positioned in a subcutaneous region under a skin surface. The method may also include advancing an external anchor a distal position toward the skin surface, and optionally, after the external anchor is positioned so as to secure the catheter in a position above the skin surface, locking the external anchor in place. In some optional implementations, the method may further include: performing a medical procedure using the intravenous cannula, after the procedure is performed, unlocking the external anchor to allow disengagement of the external anchor from the skin surface, and removing the intravenous cannula through the skin penetration point.

In some embodiments, a medical system described herein can anchor an intravenous cannula device at a skin penetration point. The system may include an intravenous cannula device and an inserter tool. The intravenous cannula device may include a proximal connector hub including a thread pattern configured to releasably connect with an external fluid line. Also, the intravenous cannula device may include a flexible catheter having a distal opening configured to provide fluid communication into a targeted vessel, and the flexible catheter may include a lumen and extending distally of the proximal connector hub to the distal opening. The intravenous cannula device may further include an external anchor device configured to be positioned along an outer wall of the flexible catheter between the distal opening of the flexible catheter and the proximal connector hub. The intravenous cannula device may optionally include a tissue anchor device, which can be positioned along the outer wall of the flexible catheter between the distal opening of the flexible catheter and the external anchor device. The inserter tool of the system can be removably coupled to the intravenous cannula device so as to insert the flexible catheter of the intravenous cannula device through a skin penetration point and into the targeted vessel. The inserter tool can include a handle and an insertion needle extending distally from the handle. The insertion needle may be slidably engaged with the lumen of the flexible catheter of the intravenous cannula device. The inserter tool may be removable from the intravenous cannula device when the insertion needle is proximally withdrawn from the lumen of the flexible catheter. The external anchor device of the intravenous cannula device may be configured to anchor the flexible catheter adjacent to and above the skin layer, and the tissue anchor device of the intravenous cannula device may be configured to anchor the flexible catheter under the skin layer when the flexible catheter of the intravenous cannula device is inserted through the skin penetration point and into the targeted vessel.

Some or all of the embodiments described herein may have one or more of the following advantages. First, some embodiments of the medical device can be configured to advantageously anchor a catheter (such as an intravenous catheter) in a selected position relative to a skin penetration point throughout the duration of using the catheter. Second, in some embodiments, a user can advantageously manipulate an intravenous catheter device in a manner that seats one or more subcutaneous anchors along an underside of the skin proximate to a skin penetration point, and then based upon the user's selected depth of insertion of the cannula, the user can customize a position of exterior anchor device to seat against an exterior of the user's skin proximate to the skin penetration point. Third, some embodiments of the device can beneficially reduce the likelihood of inadvertent inward and outward migration of the catheter cannula (such as the cannula of an intravenous catheter) through the penetration point, thereby decreasing the risk of infection or irritation at the skin penetration point. Fourth, in some implementations, the improved device can beneficially reduce the likelihood of inadvertent inward and outward migration of the catheter cannula at the vessel entry site (e.g., for a targeted located under the skin). As such, the improved device can reduce the likelihood of vessel irritation issues, such as phlebitis, thrombus formation, infiltration, and extravasation.

The details of one or more embodiments of the invention are set forth in in the accompanying drawings and the description below. Other features, objects, and advantages of the invention will be apparent from the description and drawings, and from the claims.

DESCRIPTION OF DRAWINGS

FIGS. 8A, 8B, and 8C are plan views of a spring mechanism for an external anchor of an intravenous cannula system, in accordance with some alternative embodiments.

FIG. 9 is a flow chart for an example method of utilizing an intravenous cannula having an external anchor and a subcutaneous anchor, in accordance with some embodiments.

Like reference symbols in the various drawings indicate like elements.

DETAILED DESCRIPTION OF ILLUSTRATIVE EMBODIMENTS

Figures 1A, 1B:
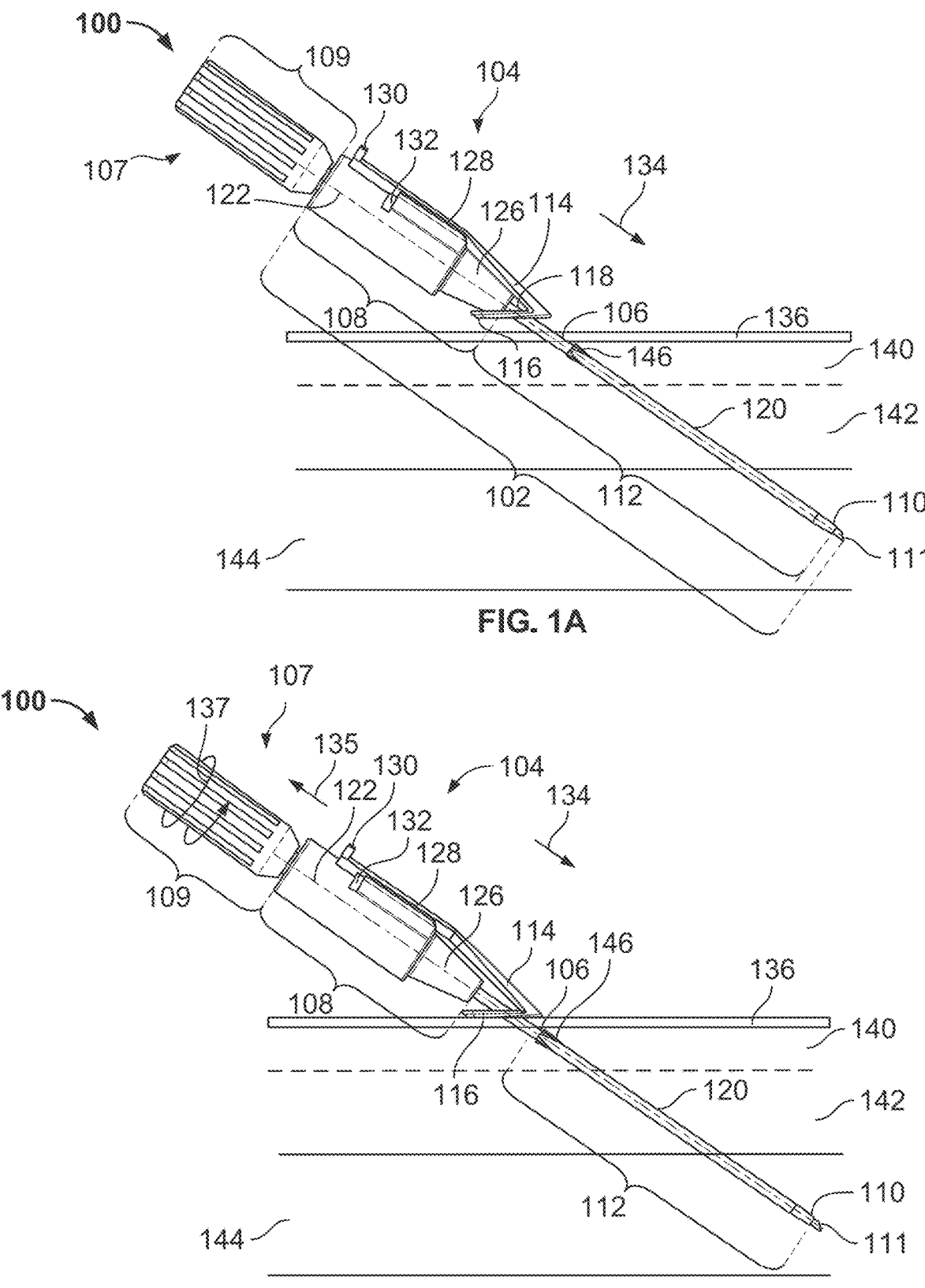
FIGS. 1A, 1B, and 1C are perspective views of an intravenous cannula system having an external anchor and a subcutaneous anchor, in accordance with some embodiments.
Figure 1C:
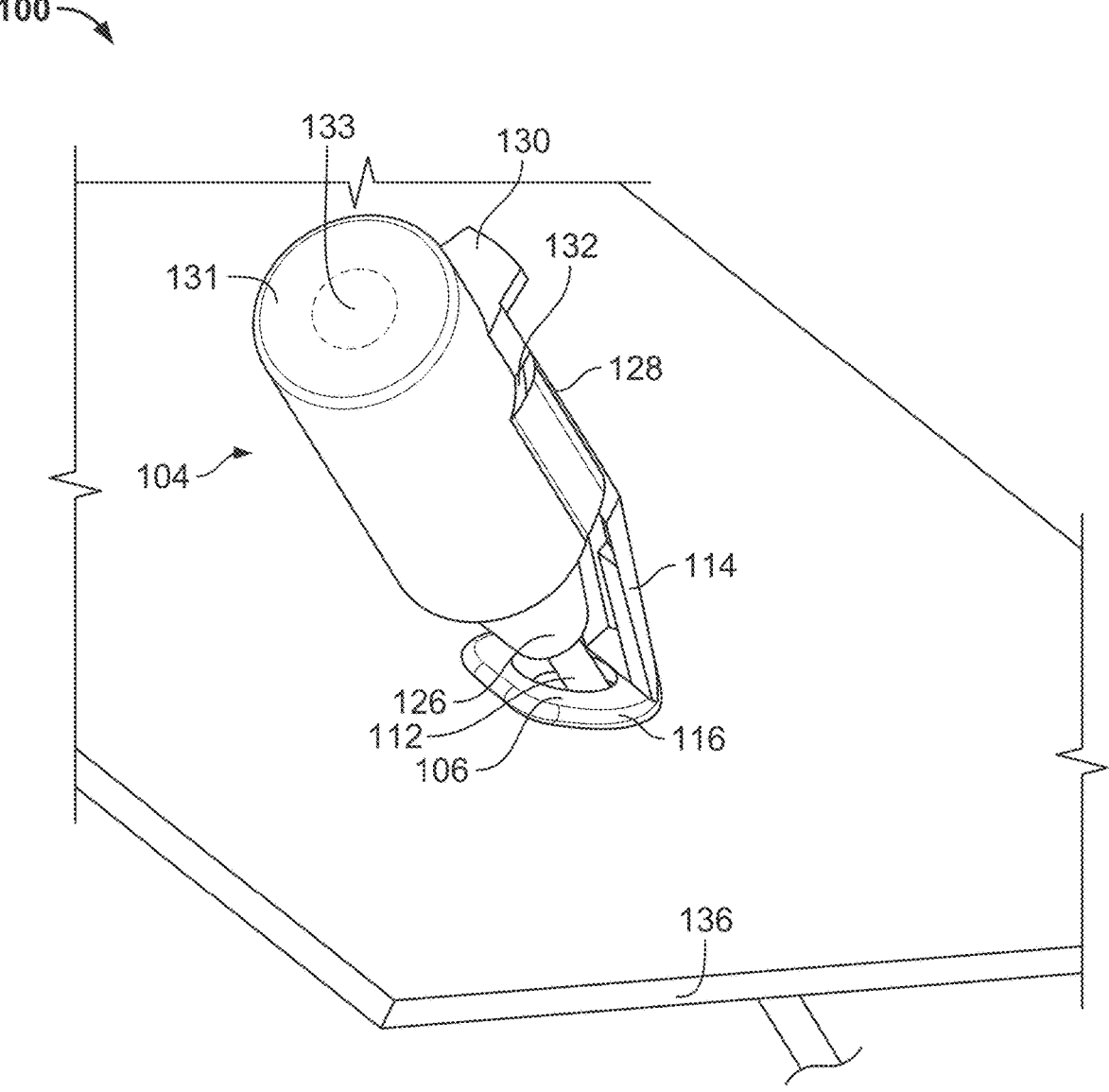

Referring to FIGS. 1A-1C, some embodiments of medical system 100 include a catheter device 102 (depicted as an intravenous cannula device in this embodiment) that is equipped with an external anchor 104 and at least one subcutaneous anchor 146 so as to secure the catheter device 102 in a position relative to a skin penetration point 106. The catheter device 102 can include a distal section having a distally extending cannula 112 (depicted as an intravenous cannula of the intravenous cannula device in this embodiment) and a proximal hub 108 configured to releasably connect with an external fluid line (not shown in FIGS. 1A-1C) or optionally configured to allow passage of a catheter 122 through the hub 108 and intravenous cannula 112. Optionally, the medical system 100 can also include an inserter tool 107 detachably connected to catheter device 102, for example, during initial penetration of the intravenous cannula device toward a targeted site in a body.

In some embodiments, the intravenous cannula 112 can include a flexible catheter 120 and a distal tip 110 which can have an opening to allow fluids, blood products, catheters, guide wires, or other medical devices to pass through the intravenous cannula 112 into a body vessel 144 of a patient. The intravenous cannula 112 can also include the subcutaneous anchor 146 extending from an exterior surface of the flexible catheter 120. The subcutaneous anchor 146 can be positioned along the flexible catheter 120 such that the subcutaneous anchor 146 is proximal to the distal tip 110 of the flexible catheter 120 and distal of the proximal hub 108. The subcutaneous anchor 146 can extend radially outward of a cylindrical wall of the flexible catheter 120 so that the subcutaneous anchor 146 engages with fatty tissue or other tissue inside the subcutaneous layer 140 immediately underlying the skin 136 near the skin penetration point 106 to provide an anchoring effect without the need for adhesives to be applied external to the skin. The subcutaneous anchor 146 includes at least one surface configured to engage an underside of the skin surface 136 or the fatty subcutaneous layer 140 when the flexible catheter 120 of the intravenous cannula 112 is inserted through the skin penetration point 106 into the targeted vessel 144. In this embodiment, the subcutaneous anchor 146 is formed as triangular barbs that are oriented to allow the flexible catheter 120 to be inserted through the skin penetration point 106 and into the desired body vessel 144, but to engage in the fatty subcutaneous layer 140 to inhibit motion of the flexible catheter 120 back through the skin penetration point 106. In other embodiments, the subcutaneous anchor 146 can be formed as one or more rings, flexible flaps, spirals, flexible tabs, tines, or barbs, and can be formed integrally with the flexible catheter 120. The subcutaneous anchor 146 can be deployable in the subcutaneous region after insertion, or can be shaped so as to easily enter through the skin penetration point 106 but to be offer resistance to withdrawing of the flexible catheter 120, for example as tabs arranged to be perpendicular to the exterior surface of the flexible catheter 120 and forming an acute angle with the exterior surface at the distal end of the tab (e.g., toward the distal tip 110 of the flexible catheter 120) and a right angle at the proximal end.

In the depicted embodiment, the hub 108 includes a generally rigid body having an outer radius that is larger than the outer radius of the flexible catheter 120, and larger than the skin penetration point 106. In this embodiment, the external anchor 104 can be movable with respect to the distal end of the hub 108, such that the external anchor 104 can be advanced toward the skin penetration point 106. In this embodiment, the external anchor 104 is movably connected to the hub 108 so that it can be extended in a distal direction from the hub 108 toward the distal tip 110 of the intravenous cannula 112. The external anchor 104 can be formed as a rigid extension 114 with a contact portion formed as a flexible ring 116 positioned at a distal end. The flexible ring 116 can at least partially surround the intravenous cannula 112, and can be positioned so as to form an angle 118 with the rigid extension 114. The angle 118 between the rigid extension 114 and the flexible ring 116 can match an angle of a distal portion of the hub 108 with respect to a hub body 126. The flexible ring 116 is the contact portion of the external anchor 104, which contacts the skin surface 136. Optionally, the flexible ring 116 can be treated with a coating of an infection-hindering composition, which would contact the skin surface 136 during use.

The external anchor 104 can also include an advancement mechanism such as an anchor advancer 128 that can be pushed forward toward a distal end of the hub body 126 by applying a force to a finger tab 130 in direction 134. The movement of the anchor advancer 128 advances the external anchor 104 distal to the end of the hub body 126 in direction 134, and can advance the flexible ring 116 along the intravenous cannula 112 until the flexible ring 116 is in contact with an exterior skin surface 136 of the patient, as shown in FIG. 1B. In some implementations, the anchor advancer 128 slides along a track with the application of force, for example, from the finger of a user. Optionally, the anchor advancer 128 moves between predetermined intervals indicated by notches or grooves in a track, so that the anchor advancer 128 can be positioned at any of multiple intervals to allow variability in the positioning of the flexible ring 116 against the skin surface 136. In some implementations, the external anchor 104 can be advanced by simply applying force to the finger tab 130 in a direction parallel to a longitudinal axis of the hub body 126. In some implementations, the external anchor 104 can be advanced by pushing down on the finger tab 130 or pinching the finger tab 130, and then applying force to the finger tab 130 in a direction parallel to a longitudinal axis of the hub body 126. In some implementations, the finger tab 130 can include ridges or other texture. In some implementations, the finger tab 130 extends perpendicularly to the hub body. In some implementations, the finger tab 130 is only slightly raised from the track anchor advancer 128 of the external anchor 104.

The external anchor 104 can be locked into place using lock 132 once it has been advanced to the desired position adjacent to the skin surface 136. In some implementations, the lock 132 is one of a tongue and groove lock, a divot lock, a slide lock, a detent, or a friction lock. For example, the lock 132 can be a friction fit between the anchor advancer 128 and the track on the hub body 126, so that the external anchor 104 can be advanced to precisely the desired position and held in place by the friction fit lock 132 without additional action by the user. In another example, the lock 132 can be notches or grooves in the track at regular intervals which the anchor advancer 128 can move between with force by the user. As will be described in greater detail below, the lock 132 can also be a helical screw, a spring, or an adhesive strip that holds the hub body 126 and the external anchor 104 in place relative to each other. In some implementations, no lock 132 is implemented, and the hub body 126 and the external anchor 104 are held in place by a friction fit or a dressing, such as surgical tape or another adhesive. Locking the hub body 126 and the external anchor 104 in place relative to one another and with the external anchor 104 in contact with the skin surface 136 stabilizes the intravenous cannula device 102 and reduces motion of the external anchor 104 relative to the skin surface 136.

Though the external anchor 104 is illustrated with rigid extension 114 supporting the flexible ring 116, in other embodiments the portion of the external anchor 104 contacting the skin surface 136 can have a different shape, such as a semi-circle or a polygon. In other embodiments, the external anchor 104 has a pair of skin-abutting feet that contact the skin on either side of the skin penetration point 106. As illustrated in FIG. 1C, for example, the flexible ring 116, formed as a circular ring that surrounds the flexible catheter 120 keeps the external anchor 104 and the proximal hub 108 centered with respect to a longitudinal axis of the intravenous cannula 112 and minimizes kinking of flexible catheter due to movement of the proximal hub 108 in a direction parallel to a plane of the skin surface 136. In some implementations, more than one rigid extension 114 can be utilized to provide additional support and stability to the flexible ring 116, for example in a preferred embodiment at least two rigid extensions attach the flexible ring 116 to the anchor advancer 128. In another embodiment, three or four rigid extensions attach the flexible ring 116 to the anchor device. The flexible ring 116 supported by one or more rigid extensions 114 maintains the visibility of the skin penetration point 106 even when the flexible ring 116 is advanced to the skin surface 136. This enables a user to view the skin penetration point 106 and to access the skin penetration point 106 if cleaning is necessary. A saline or other solution or small sponge can be inserted between the rigid extensions 114 to clean and dry the skin penetration point 106 while the intravenous cannula device 102 is held in the desired position by the external anchor 104 and subcutaneous anchor 146.

The intravenous cannula 112 can be inserted through the skin penetration point 106 at an angle, through the skin surface 136, the subcutaneous layer 140, and in some implementations, a fascia layer 142 (which may include muscle and/or its fascia), into a targeted body vessel 144. The subcutaneous anchor 146 is positioned on the intravenous cannula 112 so as to secure the intravenous cannula device 102 in a position relative to the skin penetration point 106 by engaging with the fatty tissue of the subcutaneous layer 140 along the underside of the skin. The subcutaneous anchor 146 reduces the likelihood of migration of the intravenous cannula device 102 outward through the skin penetration point 106. The external anchor 104 is advanced to abut the skin surface 136 to hinder motion of the intravenous cannula device 102 inward through the skin penetration point 106. Together, the subcutaneous anchor 146 and external anchor 104 inhibit migration of the intravenous cannula device 102 inward or outward through the skin penetration point 106. In this embodiment, a distal surface of the flexible ring 116 positioned at a distal end of the external anchor 104 is formed as a plane that is angled with respect to a plane perpendicular to the longitudinal axis of the hub body 126. The angle 118 of the flexible ring 116 enables a secure fit between the distal surface of the flexible ring 116 and the skin surface 136 when the external anchor 104 is advanced into position abutting the skin surface 136. Optionally, the proximal hub 108 may be pushed down next to the skin when a dressing is applied over the proximal hub 108, after which the subcutaneous anchor 146 and external anchor 104 cooperate on opposing sides of the skin to secure the intravenous cannula device 102 in place and to inhibit the entry of bacteria into the skin penetration point 106.

The medical system 100 depicted in FIGS. 1A-1C may optionally include an inserter tool 107 detachably coupled to the intravenous cannula device 102. The inserter tool 107 includes a handle 109 configured to be grasped by a user to control the insertion of the intravenous cannula device 102 through the skin penetration point 106 into the targeted body vessel 144. In this embodiment, the inserter tool 107 is removably coupled to the intravenous cannula device 102 such that an insertion needle 111 of the inserter tool 107 provides support to the flexible catheter 120 during insertion of the distal tip 110 of the flexible catheter 120 into the targeted body vessel 144. After the inserter tool 107 is used to facilitate the placement of the intravenous cannula device 102, the inserter tool 107 can be removed from the intravenous cannula device 102 while the distal tip 110 of the flexible catheter 120 remains in the targeted body vessel 144, providing a fluid communication line between the proximal hub 108 and the targeted body vessel 144 via the flexible catheter 120. As shown in FIG. 1C, the proximal hub 108 can include a fluid fitting 133 formed at a proximal end 131 of the proximal hub 108 configured to mate with an external fluid line. For example, the fluid fitting 133 may be configured as a luer connector in some implementations. The fluid fitting 133 can be in fluid communication with the distal tip 110 of the flexible catheter 120 through the hub body 126.

After the intravenous cannula device 102 is anchored in the operative position by the subcutaneous anchor 146 and the external anchor 104, the inserter tool 107 can be released from the intravenous cannula device 102. For example, the inserter tool 107 can be frictionally or threadably engaged with the intravenous cannula device 102. If the inserter tool 107 is frictionally engaged with the intravenous cannula device 102, the user can apply a withdrawal force to the handle 109 of the inserter tool 107 relative to the intravenous cannula device 102. If the inserter tool 107 is threadably engaged with the intravenous cannula device 102, the user can apply a rotational motion of the handle 109 of the inserter tool 107 relative to the intravenous cannula device 102. In the illustrated example in FIG. 1B, the inserter tool 107 can be released from the intravenous cannula device 102 by unscrewing, or twisting the handle 109 to apply rotational motion (illustrated as rotational direction 137) relative to the intravenous cannula device 102. Once the handle 109 has been decoupled from the intravenous cannula device 102, the inserter tool 107 can be removed by applying a withdrawal force in a direction 135 away from the proximal hub 108. While the inserter tool 107 is illustrated in FIGS. 1A and 1B only, the other embodiments of intravenous cannula devices described herein can also be implemented with an optional inserter tool 107 for purposes of initial penetration into a target body vessel 144.

Figure 2:
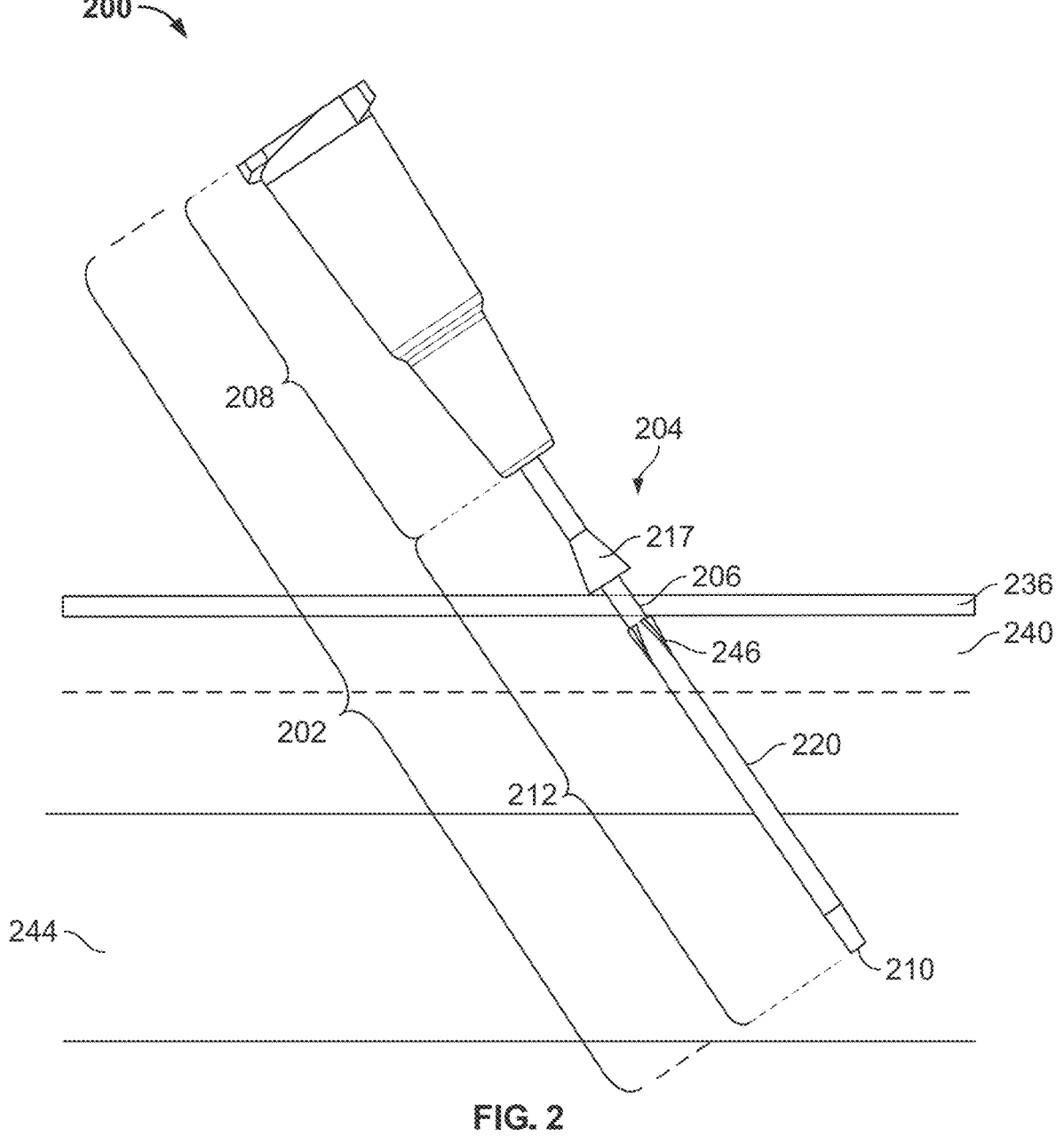
FIG. 2 is a perspective view of an intravenous cannula system having a subcutaneous anchor and an external anchor formed as an integrated part of the intravenous cannula, in accordance with some alternative embodiments.

Referring now to FIG. 2, some alternative embodiments of a medical system 200 may include both a subcutaneous anchor 246 and an external anchor 204 that are integrally attached to the side wall of the intravenous cannula 212. For example, each of the subcutaneous anchor 246 and the external anchor 204 can be formed as differently sized circumferential protrusions extending outwardly from the cannula 212. In this embodiment, the medical system 200 can be similar to the medical system 100 of FIGS. 1A-1C. For example, the medical system 200 includes an intravenous cannula device 202 having an intravenous cannula 212 and a proximal hub 208. The intravenous cannula 212 includes a flexible catheter 220 with a subcutaneous anchor 246. In this embodiment, the external anchor 204 is formed separately from the proximal hub 208 as a circumferential protrusion 217 integrally attached to the flexible catheter 220 and positioned proximal of the distal tip 210 and distal of the proximal hub 208, so as to engage with the skin surface 236. Though not shown in FIG. 2, the medical system 200 can also include an inserter tool detachably coupled to the intravenous cannula device 202 and configured to provide support to the flexible catheter 220 during placement in a targeted body vessel 244.

The circumferential protrusion 217 is formed radially about the flexible catheter 220 and has a lateral dimension on the contact surface positioned toward the skin surface 236 configured to inhibit the circumferential protrusion 217 from traveling through the skin penetration point 206. In some embodiments, the circumferential protrusion 217 is integrally formed with the flexible catheter 220, and is immovably positioned on the flexible catheter 220 so as to abut the skin surface 236 when the intravenous cannula device 202 is positioned in the targeted body vessel 244 and the subcutaneous anchor 246 is engaged in the subcutaneous layer 240 just below the skin penetration point 206. The positioning of the circumferential protrusion 217 adjacent to the skin surface 236 inhibits inward motion of the intravenous cannula device 202 through the skin penetration point 206 and stabilizes the intravenous cannula device 202 in the operable position.

Figure 3A:
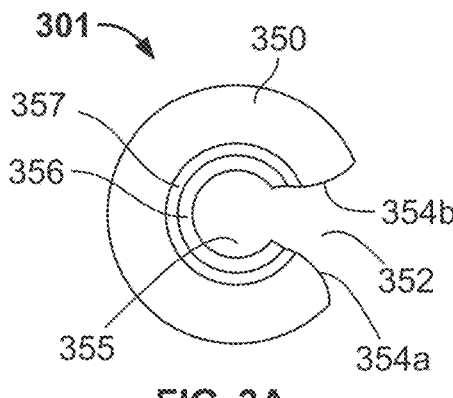
FIGS. 3A-E are perspective views of an intravenous cannula system having detachable exterior anchors and top views of the external anchors, in accordance with some alternative embodiments.
Figure 3B:
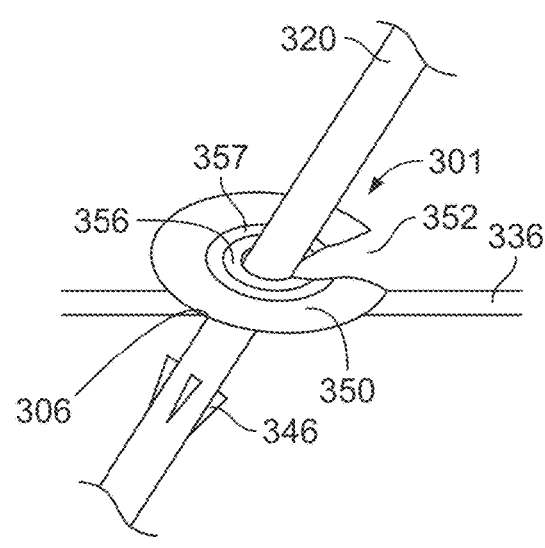

Referring to FIGS. 3A-E, some alternative embodiments of an external anchor are configured to allow placement of the anchor at a desired position on the intravenous cannula 212 to provide support and inhibit movement of the intravenous cannula system (for example, intravenous cannula system 102 of FIGS. 1A-1C or intravenous cannula device 202 of FIG. 2). For example, as shown in FIGS. 3A and 3B, the external anchor 301 can be formed as a semi-circular ring, having an outer ring protrusion 350 and an inner flange 356. The semi-circular ring 301 forms a circular conduit 355 sized to closely fit the external surface of the flexible catheter 320. The semi-circular ring 301 includes a gap 352 formed between edges 354a and 354b that allows the semi-circular ring 301 to be placed on the flexible catheter 320. In some embodiments, the semi-circular ring 301 can be formed of a flexible material so that the gap 352 can be deformed by moving the edges 354a and 354b relative to one another to allow the flexible catheter 320 to pass through the deformed gap 352. In some embodiments, the gap 352 is sized to allow passage of the flexible catheter 320 through the gap 352 without deformation of the gap 352. In some embodiments, the outer ring protrusion 350 is formed from a flexible or rigid polymer. The outer ring protrusion 350 can be coupled to the inner flange 356 by a transitional region 357, which can include an additional material to transition from the polymer of the outer ring protrusion 350 to the inner flange 356. In some embodiments, one side of the semi-circular ring 301 can have a different shape than the other side, to better form a flat contact surface with a skin surface 336. In other embodiments, both sides can be substantially the same such that either side can be in contact with the skin surface 336. The inner flange 356 abuts the flexible catheter 320 when the semi-circular ring 301 is positioned on the flexible catheter 320. The inner flange 356 can be formed from a material that provides a frictional fit with the outer surface of the flexible catheter 320 to keep the semi-circular ring 301 in a desired position along the surface of the flexible catheter 320 without exerting an occluding force on the flexible catheter 320 (e.g., without squeezing or pinching the flexible catheter in a manner that impairs the intended catheter performance). Also, as with the other skin-contacting structures described herein, the inner flange 356 can be formed from a biocompatible material and optionally can be coated with an anti-bacterial coating for purposes of reducing the likelihood of infection.

The semi-circular ring 301 can be positioned on the flexible catheter 320 so as to abut the skin surface 336 near the skin penetration point 306. The outer ring protrusion 350 has a diameter greater than the skin penetration point 306 so that the semi-circular ring 301 cannot enter the skin penetration point 306. The semi-circular ring 301 inhibits an inward motion of the flexible catheter 320 through the skin penetration point 306. The subcutaneous anchor 346 of the flexible catheter 320 simultaneously inhibits outward motion of the flexible catheter 320.

Figure 3C:
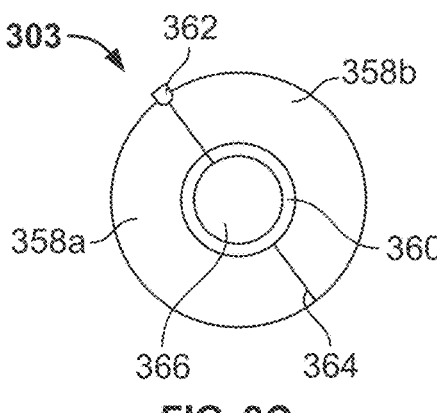
Figure 3D:
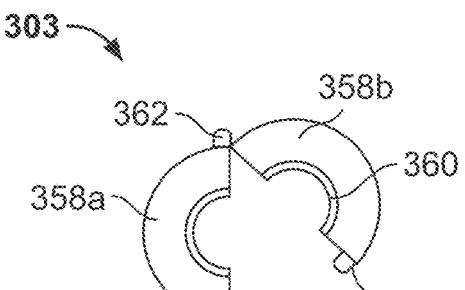
Figure 3E:
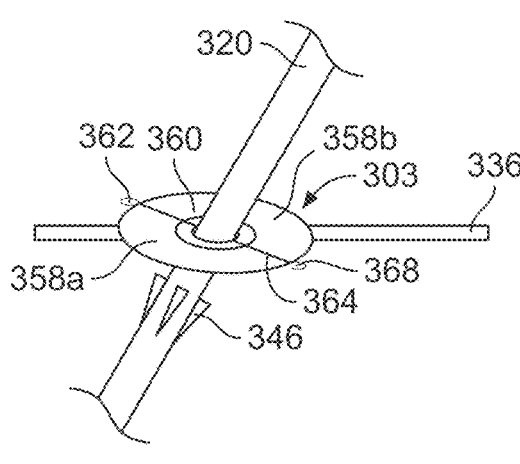

Referring now to FIGS. 3C-3E, in some embodiments the external anchor 303 can be formed as a clamp that removably attaches to an exterior of the hub or intravenous cannula at a user-selected position. For example, the external anchor 303 can be formed as a clamp having first and second semi-circular arms 358a and 358b, coupled by a hinge 362, and having an opening side 364. The clamp 303 can include an inner flange 360 that surrounds the circular conduit 366 formed when the first and second semi-circular arms 358a and 358b are in a closed configuration, as shown in FIG. 3C. In some embodiments, the hinge 362 is biased to the closed configuration. For example, the hinge 362 can include a spring or can be a living hinge which returns to the closed configuration when no force is exerted on the first and second semi-circular arms 358a and 358b to keep them in an open configuration. In some embodiments, the hinge 362 is unbiased. For example, the hinge 362 can remain open without the exertion of force on the first and second semi-circular arms 358a and 358b. The clamp 303 can further include a lock 368 to secure the first and second semi-circular arms 358a and 358b in the closed configuration after the flexible catheter 320 has been inserted into the circular conduit 366. The inner flange 360 can provide a frictional force against the exterior surface of the flexible catheter 320, so that the clamp 303 is secured in a desired position on the flexible catheter 320 without occluding the flexible catheter 320 by the force (e.g., without squeezing or pinching the flexible catheter in a manner that impairs the intended catheter performance).

As illustrated in FIG. 3E, the clamp 303 is positioned on the flexible catheter 320 so as to abut the skin surface 336. The first and second semi-circular arms 358a and 358b can be opened at the opening side 364, positioned on the flexible catheter 320 so that the flexible catheter 320 is within the circular conduit 366 formed by the first and second semi-circular arms 358a and 358b when the clamp 303 is closed. The first and second semi-circular arms 358a and 358b can be locked together with lock 368, or as described above, in some embodiments the first and second semi-circular arms 358a and 358b are biased to a closed configuration. As such, the clamp 303 is retained along the exterior of the catheter 320 and serves as a stopper that resides entirely exterior to the skin for purposes of hindering forward migration of the catheter further into the skin penetration point 306. The subcutaneous anchor 346 of the flexible catheter 320 secures the flexible catheter 320 in the subcutaneous tissue under the skin surface 336 and the clamp 303 positioned above the skin surface 336 to inhibit movement of the flexible catheter 320 through the skin penetration point 306.

Figures 4A, 4B:
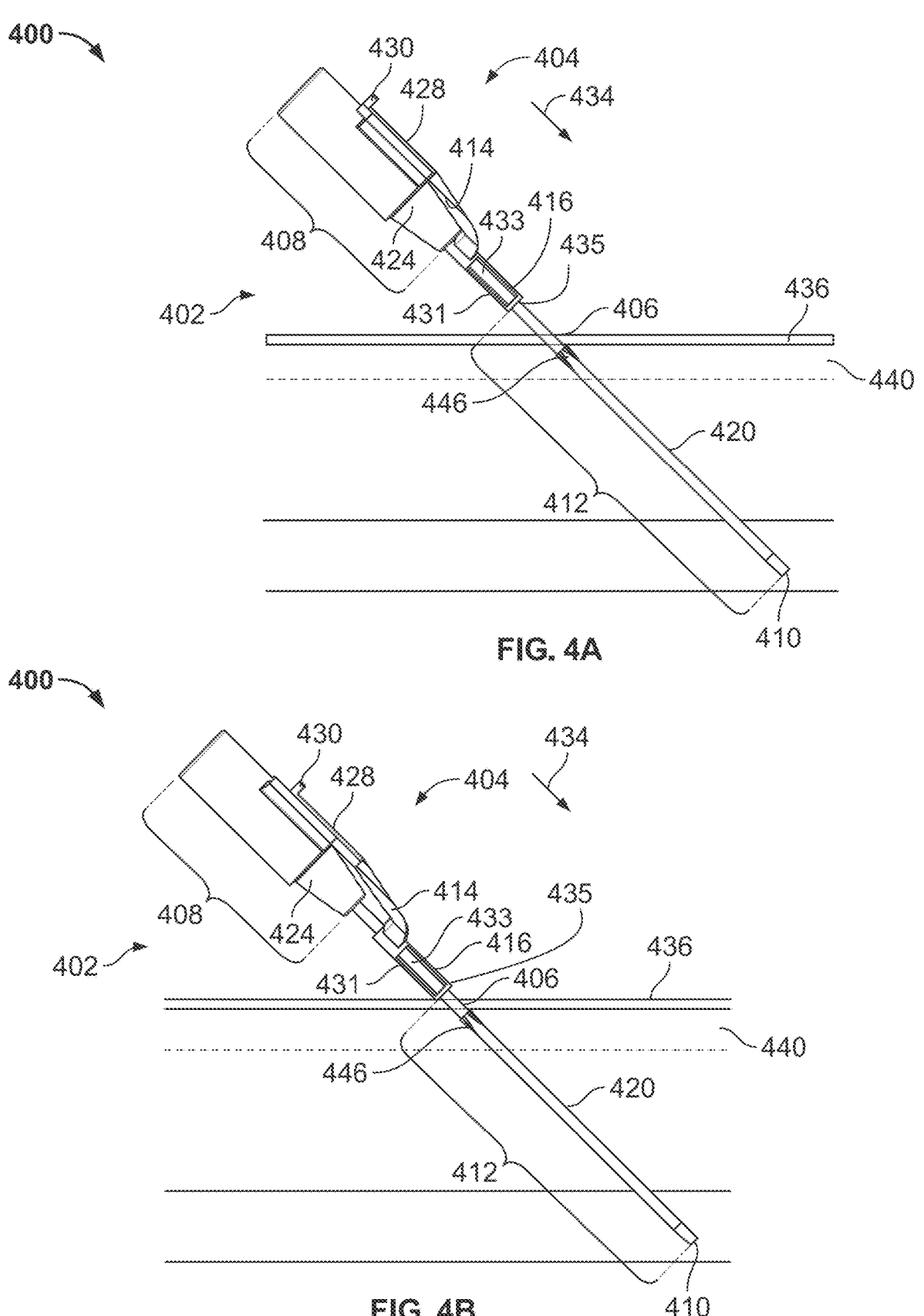
FIGS. 4A and 4B are perspective views of an intravenous cannula system having an advanceable external anchor formed as a cage about the intravenous cannula and a subcutaneous anchor, in accordance with some alternative embodiments.

Referring now to FIGS. 4A and 4B, some alternative embodiments of a medical system 400 can include a subcutaneous anchor 446 and an external anchor 404 which is advanced from the proximal hub 408, and includes for example, a cage structure 416 about the flexible catheter 420. In this embodiment, the medical system 400 can be similar to medical system 100 of FIGS. 1A-C and medical system 200 of FIG. 2. For example, medical system 400 includes an intravenous cannula device 402 with an intravenous cannula 412 and a proximal hub 408. The intravenous cannula 412 includes a flexible catheter 420 and subcutaneous anchor 446. The proximal hub 408 also includes the external anchor 404 including a circumferential cage 416 movably coupled to the proximal hub 408 by rigid extension 414 so that the circumferential cage 416 can be extended in a distal direction from the proximal hub 408 along the flexible catheter 420 to engage with a skin surface 436. The distal end contact surface of the circumferential cage 416 engages with the skin surface 436 to hold the intravenous cannula device 402 in place and reduce likelihood of migration of the intravenous cannula device 402 inward at the skin penetration point 406, while the subcutaneous anchor 446 engages with the subcutaneous layer 440 below the skin surface 436 to reduce likelihood of migration of the intravenous cannula device 402 outward through the skin penetration point 406.

In this embodiment, the circumferential cage 416 of the external anchor 404 can be formed about the flexible catheter 420 from a plurality of scaffolds 431. In some embodiments, the scaffolds 431 can extend down the flexible catheter 420 parallel to a longitudinal axis of the flexible catheter 420 and be joined to a circumferential ring 435 through which the flexible catheter 420 extends. The scaffolds 431 and circumferential ring 435 form a cylindrical cage with openings 433 through which the flexible catheter 420 can be accessed or viewed. The circumferential cage 416 can also include an advancement mechanism such as an anchor advancer 428 that can be pushed forward from the proximal hub 408 toward the distal portion 424 of the proximal hub 408. The anchor advancer 428 is coupled to the circumferential cage 416 by rigid extension 414, which advances the circumferential cage 416 along the flexible catheter 420 toward the distal tip 410. The anchor advancer 428 can be pushed forward by applying a force to a finger tab 430 in direction 434 until a distal end of the circumferential cage 416 is in contact with the skin surface 436 of the patient as shown in FIG. 4B. As described above, the anchor advancer 428 can be advanced along the proximal hub by a variety of mechanisms, including, for example, a track having notches or grooves at various intervals or having a stop at a particular position. The anchor advancer 428 can optionally further be locked into a position by a lock mechanism, as described above.

The distal portion of the circumferential cage 416 can be advanced until it is in a desired position along a length of the flexible catheter 420, preferably abutting an external surface of the skin 436. As described above, a variety of mechanisms can be used to lock the circumferential cage 416 in a desired position (lock not shown in FIGS. 4A and 4B). The placement of the circumferential cage 416 at the skin surface 436 hinders inward motion of the intravenous cannula 412 through the skin penetration point 406, while the subcutaneous anchor 446 engages with the subcutaneous tissue 440 below the skin surface 436 to reduce any outward motion of the intravenous cannula 412. The circumferential cage 416 and the subcutaneous anchor 446 stabilize a position of the intravenous cannula device 402 relative to the surface of the skin 436 and reduce the likelihood of inward or outward movement of the intravenous cannula device 402 through the skin penetration point 406, reducing introduction of bacteria to the body and minimizing occurrence of vessel trauma. The scaffolds 431 and circumferential ring 435 forming the circumferential cage 416 provide openings 433 in the cage structure that enable a medical professional to monitor the skin penetration point 406 visually, and to apply cleaning solutions to the skin penetration point 406.

Figures 5A, 5B:
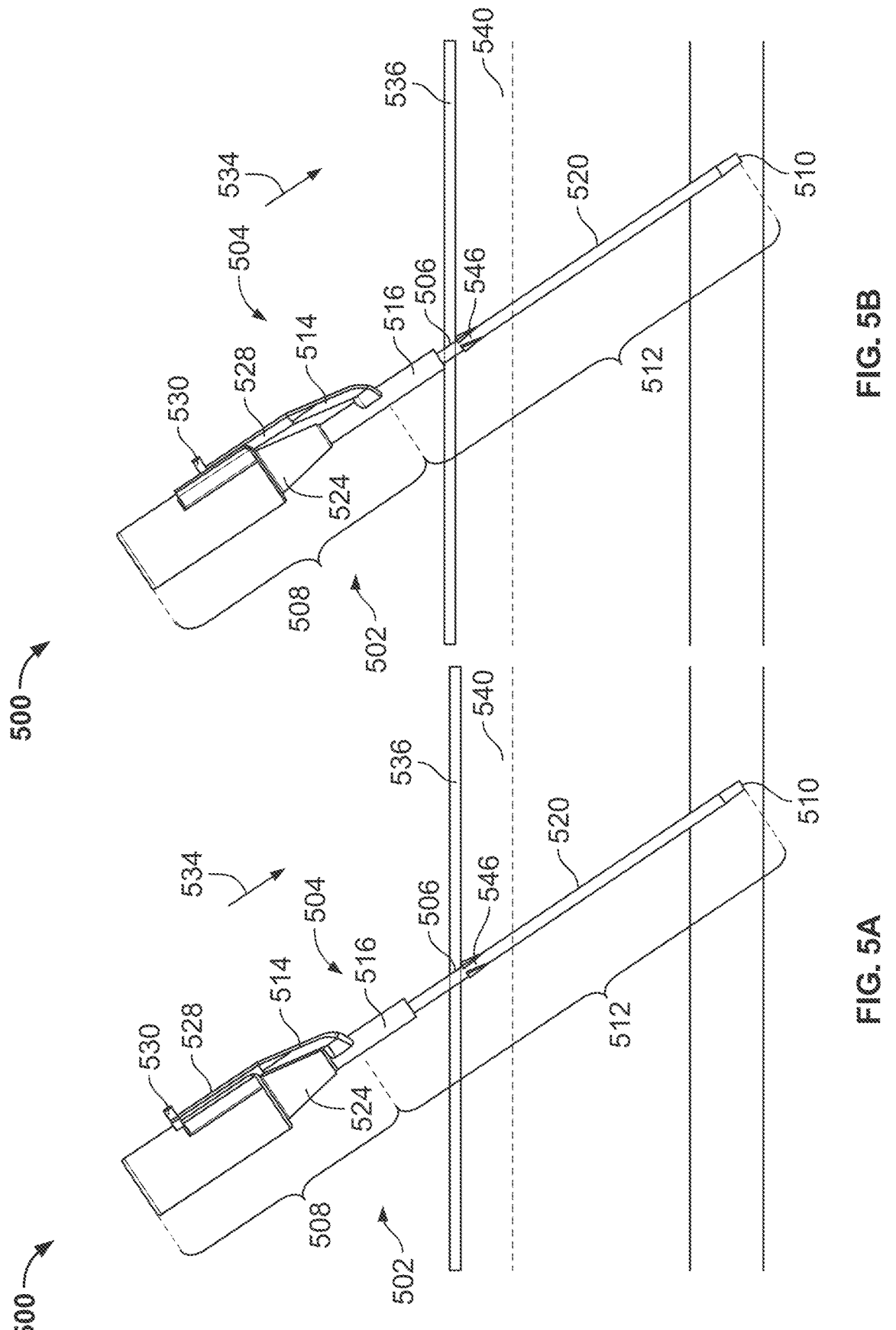
FIGS. 5A and 5B are perspective views of an intravenous cannula system having an advanceable external anchor formed as a flexible covering about the intravenous cannula and a subcutaneous anchor, in accordance with some alternative embodiments.

Referring now to FIGS. 5A and 5B, some alternative embodiments of a medical system 500 may include a subcutaneous anchor 546 and an external anchor 504, which can include a sleeve structure positioned about an intravenous cannula 512 and advanceable from the proximal hub 508. In this embodiment, the medical system 500 can be similar to medical system 100 of FIGS. 1A-C, medical system 200 of FIG. 2, and medical system 400 of FIG. 4. For example, medical system 500 includes an intravenous cannula device 502 having a proximal hub 508 and the intravenous cannula 512 including a flexible catheter 520 and subcutaneous anchor 546. The medical system 500 also includes an external anchor 504 including the circumferential sleeve 516 about the flexible catheter 520 and movably coupled to the proximal hub 508 so that the circumferential sleeve 516 can be extended in a distal direction 534 from the proximal hub 508 along the flexible catheter 520 to engage with a skin surface 536. A distal portion of the circumferential sleeve 516 contacts and engages with the skin surface 536 to hold the intravenous cannula device 502 in place and reduce motion of the intravenous cannula device 502 inward at the skin penetration point 506, while the subcutaneous anchor 546 engages with the subcutaneous layer 540 below the skin surface 536 to reduce the occurrence of outward motion of the intravenous cannula device 502.

In this embodiment, the circumferential sleeve 516 can be formed as a cylindrical tube surrounding the flexible catheter 520 proximal to the proximal hub 508. The cylindrical tube can be sized to reduce ingress of blood through the circumferential sleeve 516 and into the proximal hub 508. For example, in some embodiments, the cylindrical tube of the sleeve 516 can be sized such that any gap between an interior surface of the cylindrical tube and an exterior wall of the flexible catheter 520 is minimized. Additionally or alternatively, the cylindrical tube can include an o-ring or other barrier to fluid ingress into the circumferential sleeve 516. In some embodiments, the proximal hub 508 also includes one or more o-rings or other barriers to fluid ingress.

The external anchor 504 can also include an advancement mechanism for the sleeve 516, such as an anchor advancer 528 that can be pushed forward in a distal direction from the proximal hub 508 toward the distal portion 524 of the proximal hub 508 and along the flexible catheter 520 toward the distal tip 510. As described above, the anchor advancer 528 can be pushed forward by applying a force to a finger tab 530 in direction 534, to advance the rigid extension 514 coupled to the circumferential sleeve 516, until a distal end of the circumferential sleeve 516 is in contact with the skin surface 536 of the patient as shown in FIG. 5B. The anchor advancer 528 can be advanced along the proximal hub by a variety of mechanisms, including, for example, a track having notches or grooves at various intervals or having a stop at a particular position as described herein. The anchor advancer 528 can optionally further be locked into a position by a lock mechanism, as described above.

The distal portion of the circumferential sleeve 516 can be advanced along the flexible catheter 520 until it is in a desired position, preferably abutting an external surface of the skin 536. The circumferential sleeve 516 inhibits inward motion of the intravenous cannula 512 through the skin penetration point 506, while the subcutaneous anchor 546 engages with the subcutaneous tissue 540 below the skin surface 536 to inhibit an outward motion of the intravenous cannula 512. The circumferential sleeve 516 and the sub-cutaneous anchor 546 stabilize a position of the intravenous cannula device 502 relative to the surface of the skin 536 and minimize further inward or outward motion of the intrave-nous cannula device 502 reducing introduction of bacteria to the body. The circumferential sleeve 516 can be formed so as to protect the flexible catheter 520 from kinking, for example the circumferential sleeve 516 can be formed from a flexible material which conforms to a curve of the flexible catheter 520 when the proximal hub 508 is laid against the skin surface 536.

Figures 6A, 6B:
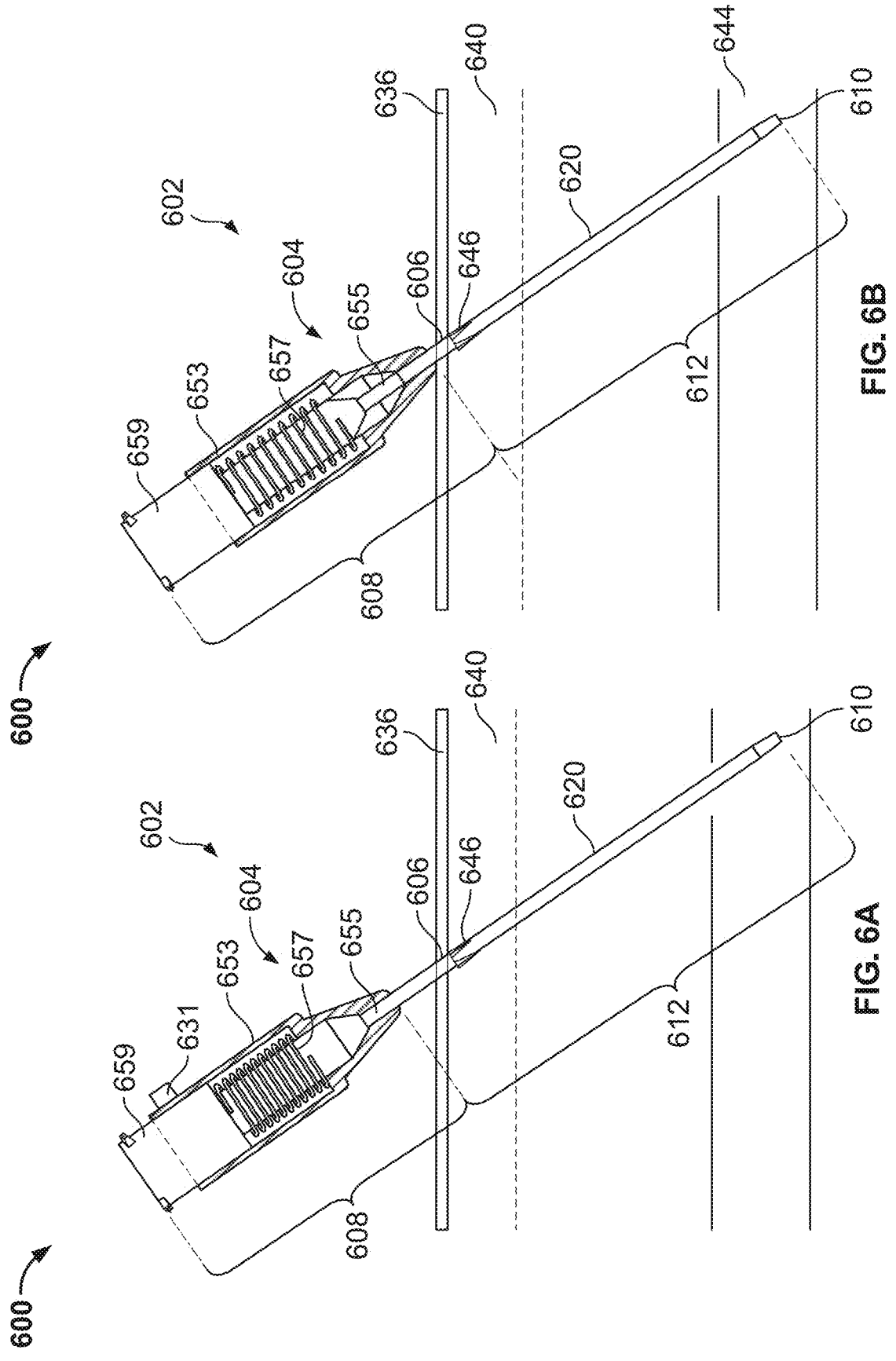
FIGS. 6A and 6B are perspective views of an intravenous cannula system having an external anchor advanced by spring tension and a subcutaneous anchor, in accordance with some alternative embodiments.

Referring to FIGS. 6A and 6B, some alternative embodi-ments of a medical system 600 may include a subcutaneous anchor 646 and an external anchor 604 formed as a movable portion of the proximal hub 608 that can be advanced along the flexible catheter 620 by a spring 657. In this embodi-ment, the medical system 600 can be similar to medical system 100 of FIGS. 1A-C, medical system 200 of FIG. 2, medical system 400 of FIG. 4, and medical system 500 of FIG. 5A-B. For example, medical system 600 includes an intravenous cannula device 602 having a proximal hub 608 and an intravenous cannula 612. The intravenous cannula 612 includes a flexible catheter 620 and subcutaneous anchor 646. The medical system 600 also includes an external anchor formed as a sliding proximal portion 604 of the proximal hub 608 that can be advanced distal of the proximal hub 608 along the flexible catheter 620 toward the distal tip 610 to engage with a skin surface 636. The sliding proximal portion 604 of the proximal hub 608 engages with the skin surface 636 to hold the intravenous cannula device 602 in place and inhibit inward motion of the intravenous cannula device 602 at the skin penetration point 606, while the subcutaneous anchor 646 engages with the subcutaneous layer 640 below the skin surface 636 to minimize outward motion of the intravenous cannula device 602 through the skin penetration point 606.

In this embodiment, the sliding proximal portion 604 of the proximal hub 608 can be formed as an outer distal covering 653 of the proximal hub 608, which can move forward along the flexible catheter 620 relative to the proximal portion 659 of the proximal hub 608. The outer distal covering 653 can be formed as a cylinder concentric with the proximal portion 659 of the proximal hub 608. In this embodiment, a proximal region of the outer distal covering 653 can cover the proximal portion 659 of the proximal hub 608, and an opening 655 in a distal region of the outer distal covering 653 allows the flexible catheter 620 to pass through. In other embodiments, the outer distal covering 653 can extend under a portion of the proximal hub 608.

The outer distal covering 653 of the sliding proximal portion 604 houses a helical spring 657 that has a com-pressed state in which the spring tension is high, as shown in FIG. 6A. The spring 657 can be released to advance the outer distal covering 653 along the flexible catheter 620 toward the skin surface 636, as shown in FIG. 6B. The spring tension of the spring 657 can hold a distal contact surface of the outer distal covering 653 against the skin surface 636, without exerting too great an outward force on the subcutaneous anchor 646.

Various mechanisms can be used to release the spring 657 to advance the sliding proximal portion 604 toward the skin surface 636. For example, in this embodiment, a button 631 can extend from an outer surface of the proximal portion 659 of the proximal hub 608 through an opening in the outer distal covering 653. The button 631 can hold the outer distal covering 653 in place relative to the proximal hub 608 and holds the spring in the compressed state until the button 631 is pressed in to release the spring 657. The spring tension of spring 657 and length of spring 657 in the released state can be chosen so that a distal end of the outer distal covering 653 abuts the skin surface 636. As described above, a lock can be used to lock the sliding proximal portion 604 in place. In this embodiment, the sliding proximal portion 604 is con-figured to be lockless and held in place by the released spring 657. In some embodiments, an adhesive dressing placed over the intravenous cannula device 602 can function as a lock to retain the sliding proximal portion 604 adjacent to the skin surface 636 to inhibit migration of the intrave-nous cannula device 602 through the skin penetration point 606.

The opening 655 in the outer distal covering 653 can be sized to minimize ingress of blood through the opening 655 and into the proximal hub 608. For example, in some embodiments, the opening 655 is sized such that any gap between an interior surface of the outer distal covering 653 at the opening 655 and an exterior wall of the flexible catheter 620 is minimized. Additionally or alternatively, the sliding proximal portion 604 can include an o-ring or other barrier at the opening 655 to fluid ingress into the proximal hub 608. The ingress of blood can also be inhibited with the decreased occurrence of inward and outward motion of the intravenous cannula 612 as provided by the sliding proximal portion 604 and subcutaneous anchor 646.

Figures 7A, 7B:
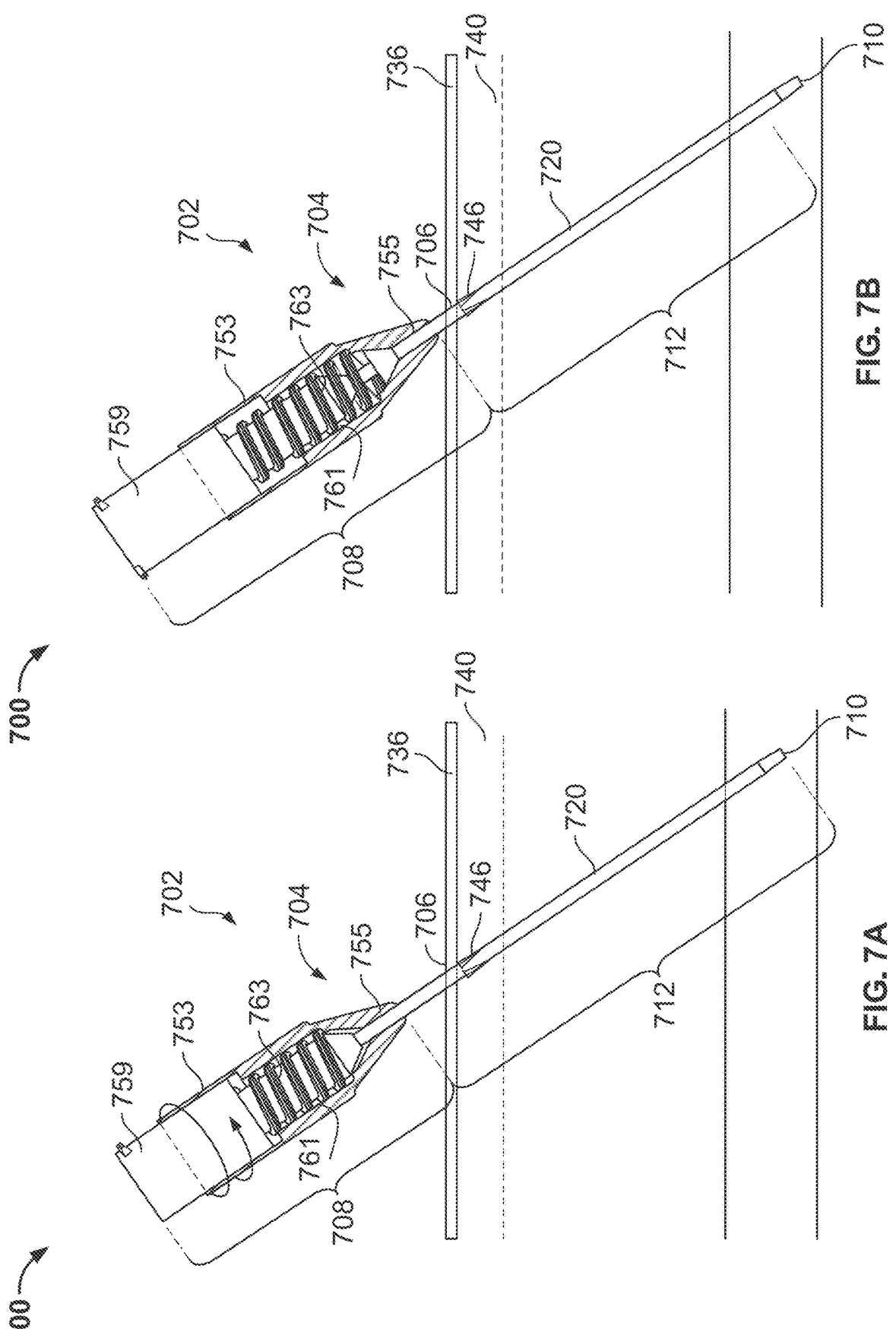
FIGS. 7A and 7B are perspective views of an intravenous cannula system having an external anchor advanced on threads and a subcutaneous anchor, in accordance with some alternative embodiments.

Referring to FIGS. 7A and 7B, some alternative embodi-ments of a medical system 700 may include a subcutaneous anchor 746 and a threaded external anchor 704 formed as a portion of the proximal hub 708 that can be advanced along the flexible catheter 720 with a rotational motion. In this embodiment, the medical system 700 can be similar to medical system 100 of FIGS. 1A-C, medical system 200 of FIG. 2, medical system 400 of FIG. 4, medical system 500 of FIG. 5, and medical system 600 of FIG. 6. For example, medical system 700 includes an intravenous cannula device 702 having a proximal hub 708 and an intravenous cannula 712 including a flexible catheter 720 with distal tip 710 and subcutaneous anchor 746. The medical system 700 also includes an external anchor formed as a sliding proximal portion 704 of the proximal hub 708 that can be advanced distal of the proximal hub 708 along the flexible catheter 720 to engage with a skin surface 736. The sliding proximal portion 704 of the proximal hub 708 contacts and engages with the skin surface 736 to hold the intravenous cannula device 702 in place and inhibit motion of the intravenous cannula device 702 inward at the skin penetration point 706, while the subcutaneous anchor 746 engages with the subcutaneous layer 740 below the skin surface 736 to reduce outward motion of the intravenous cannula device 702 through the skin penetration point 706.

In this embodiment, the sliding proximal portion 704 can be formed as an outer distal covering 753 of the proximal hub 708, which can move forward along the flexible catheter 720 relative to the proximal portion 759 of the proximal hub 708. The outer distal covering 753 can be formed as a cylinder concentric with the proximal portion 759 of the proximal hub 708. In this embodiment, a proximal region of the outer distal covering 753 can cover the proximal portion 759 of the proximal hub 708, and an opening 755 in a distal region of the outer distal covering 753 allows the flexible catheter 720 to pass through. In other embodiments, the outer distal covering 753 can extend under a portion of the proximal hub 708.

The outer distal covering 753 of the sliding proximal portion 704 includes on an internal surface internal threads 761 and houses a threaded screw 763. The threaded screw 763 is fixedly coupled to the proximal portion of the hub 708 so that the catheter 720 fixedly coupled to the threaded screw 763 and the proximal portion of the hub 708. The sliding proximal portion 704 is advanced along the flexible catheter 720 by applying a relative rotational motion to move the internal threads 761 along the threaded screw 763. For example, the rotational motion is applied to the distal covering 753 relative to proximal portion 759 of the proximal hub 708, as shown in FIG. 7A, in order to advance the sliding proximal portion 704 towards the skin surface 736, as shown in FIG. 7B. As such, the rotational motion would be applied to the distal covering 753 while the proximal portion of the hub 708 can remain stationary to thereby maintain the catheter 720 in a rotationally stationary position while in the targeted body site.

The sliding proximal portion 704 can be advanced on the internal threads 761 along the length of the flexible catheter 720 until a distal end of the sliding proximal portion is in a desired position, preferably abutting the skin surface 736. The sliding proximal portion 704 then holds the intravenous cannula 712 in place and inhibits motion of the flexible catheter 720 inward at the skin penetration point 706. The subcutaneous anchor 746 simultaneously engages the subcutaneous tissue 740 under the skin surface 736 to inhibit outward motion of the flexible catheter 720 through the skin penetration point 706. The position of the distal end of the sliding proximal portion 704 is changeable by the application of rotational motion, but does not move in a forward or backward direction along the flexible catheter 720 in the absence of such motion. As described above, an o-ring or other barrier at the opening 755 can minimize fluid ingress into the proximal hub 708.

Referring now to FIGS. 8A-8B, in some alternative embodiments, an external anchor system 801 is formed from a non-traditional spring mechanism 871. The external anchor system 801 includes a hub portion 860 forming a cavity 866 into which flexible catheter 864 extends. The hub portion 860 includes the non-traditional spring mechanism 871 having first spring 870a and second spring 870b. Sliding anchor 862 is formed as a securement tube or cylinder having an indented portion 875, which is optionally located along a central region of the anchor 862. The sliding anchor 862 can slide into the cavity 866 of hub portion 860, and through which flexible catheter 864 extends. First spring 870a is retained at a spring hinged end 872a to a wall of the hub portion 860, and is retained at a pivotable end 876a to the sliding anchor 862. Between the spring hinged end 872a and the pivotable end 876a is a non-spring hinge 874a. Similarly, the second spring 870b included a spring hinged end 872b coupled to the hub portion 860, a pivotable end 876b coupled to the sliding anchor 862, and a non-spring hinge 874b positioned between the spring-hinged end 872b and pivotable end 876b.

In this embodiment, the pivotable end 876a of the first spring 870a and the pivotable end 876b of the second spring 870b are coupled to the sliding anchor 862 at the indented center portion 875, and are pivotable within angled walls of the indented center portion 875. Springs 870a and 870b hold the sliding anchor 862 in a contracted or retracted state (e.g., FIG. 8A) until the non-spring hinges 874a and 874b are forced beyond an inflection point by the application of a force on the sliding anchor 862 in a forward direction 868 toward the distal end of the hub portion 860 and along the flexible catheter 864. FIG. 8B shows the springs 870a and 870b at the inflection point, with non-spring hinges 874a and 874b positioned such that the pivotable ends 876a and 876b are at about a 90° angle to a surface of the sliding anchor 862 at the indented center portion 875. FIG. 8C shows the springs 870a and 870b forced beyond the inflection point, such that the non-spring hinges 874a and 874b now maintain the sliding anchor 862 in an advanced or extended state. In the extended state, the sliding anchor 862 is extended outward from a distal end of the hub portion 860 along the flexible catheter 864. In the extended state, the distal end of the sliding anchor 862 can be positioned adjacent to the skin surface (not shown) so as to support and maintain an intravenous cannula with respect to a skin penetration point, in conjunction with internal anchors engaged in the subcutaneous tissue (not shown). In some embodiments, guide markings on the flexible catheter 864 can illustrate the distance that the sliding anchor 862 extends from the hub portion in the extended state, to aid in positioning.

Referring to FIG. 9, one example method 900 provides a variety of operations to deliver an intravenous cannula into a body vessel for use in a medical procedure. The method of FIG. 9 may be implemented with all embodiments of the medical systems and intravenous cannula devices described above. At step 902, a distal portion of an intravenous cannula is inserted into a skin penetration point of a patient. As described above in FIGS. 1A-C, an inserter tool can be used with the intravenous cannula device to provide support to a flexible catheter during insertion through the skin penetration point and into a targeted vessel. At step 904, the intravenous cannula device is advanced until the distal end of the device enters the targeted body vessel and at least one subcutaneous anchor is positioned in the subcutaneous layer below the skin. The subcutaneous anchor engages with the subcutaneous layer to inhibit motion of the intravenous cannula device out of the skin penetration point.

At step 906, an external anchor is engaged to secure the intravenous cannula in a position above the surface of the skin. The external anchor can be any of the anchors described above in FIGS. 1-8. For example, in some embodiments, such as those described in FIGS. 1A-C, 4A-B, and 5A-B, the external anchor can be coupled to the proximal hub and is engaged by the user sliding an advancer mechanism in the direction of the distal end of the proximal hub. In other embodiments, such as those described in FIGS. 6A-B, the external anchor is engaged by a spring mechanism or, as described in FIGS. 7A-B, by the user applying a rotational motion to an internal screw of the proximal hub to extend the internal anchor along the flexible catheter. In some embodiments, such as those described in FIGS.

3A-3E, the external anchor is a clamp or semicircular ring that can be positioned on the flexible catheter at any desired position. In some embodiments, such as those described in FIG. 2, the external anchor is circumferential protrusion is formed radially about the flexible catheter, and the circumferential protrusion is engaged by advancing the flexible catheter through the skin penetration point until the circumferential protrusion abuts the skin surface. Once the external anchor is engaged with the skin surface, the external anchor can optionally by locked in place by a lock mechanism.

In step 908, after the procedure is completed, the external anchor can be optionally disengaged so that it can be moved back toward the proximal hub and away from the surface of the skin. (Alternatively, the external anchor may remain in its position relative to the catheter wall during withdrawal of the catheter from the skin.) If the external anchor was locked in place, the lock can also be disengaged prior to movement of the external anchor along the flexible catheter. Finally, at step 910, the intravenous cannula device can be removed from the patient through the skin penetration point.

A number of embodiments of the invention have been described. Nevertheless, it will be understood that various modifications may be made without departing from the scope of the invention. Accordingly, other embodiments are within the scope of the following claims.

What is claimed is:

1. A medical system for anchoring an intravenous cannula device with respect to a skin surface, the system comprising:
   a proximal hub comprising:
   a hub body having a proximal end, a distal end, and a longitudinal axis extending from the proximal end to the distal end; and
   an intravenous cannula comprising:
   a flexible catheter having an exterior circumferential surface configured to extend through a skin penetration point into a target body vessel, the flexible catheter extending distally of the proximal hub to a distal opening at a distal end of the flexible catheter; and
   a tissue anchor device positioned on an exterior surface of the flexible catheter between the distal opening and the distal end of the hub; and
   an external anchor device movably coupled along the longitudinal axis to the hub body, the external anchor device configured to at least partially surround the flexible catheter, wherein the external anchor device defines a stopper element with a lateral dimension greater than the exterior circumferential surface of the flexible catheter; and
   wherein the tissue anchor device is configured to anchor under a skin layer of a patient and the external anchor device is configured to be positioned distal to the hub body and proximal of the tissue anchor device such that the external anchor device is adjacent to the skin surface.

2. The system of claim 1, wherein the external anchor device is formed as an integral part of the hub body, extending distal of the hub body about the flexible catheter.

3. The system of claim 2, wherein the external anchor device is formed as a protrusion from the hub body, and the protrusion has a flat surface configured to mate with the skin surface.

4. A medical system for anchoring an intravenous cannula device with respect to a skin surface, the system comprising:
   a proximal hub comprising:
   a hub body having a proximal end, a distal end, and a longitudinal axis extending from the proximal end to the distal end; and an external anchor device movably coupled along the longitudinal axis to the hub body and configured to at least partially surround a flexible catheter, the external anchor device having an advancement mechanism and a contact portion, the contact portion having a lateral dimension greater than a diameter of a skin opening dimension defined by the flexible catheter, and the external anchor device configured to be advanced in a direction of the longitudinal axis of the hub body along the flexible catheter; and
an intravenous cannula comprising:
the flexible catheter configured to extend through a skin penetration point and define the skin opening dimension, the flexible catheter extending distally of the proximal hub to a distal opening at a distal end of the flexible catheter; and
a tissue anchor device positioned on an exterior surface of the flexible catheter between the distal opening and the distal end of the hub; and
wherein the tissue anchor device is configured to anchor under a skin layer of a patient and the external anchor device is configured to be positioned distal of the hub body and proximal of the tissue anchor device such that the external anchor device is adjacent to the skin surface.

5. The system of claim 4, wherein upon application of a force to the advancement mechanism in a direction parallel to the longitudinal axis, the contact portion is advanced distal of the distal end of the hub body along the flexible catheter.

6. The system of claim 5, wherein the contact portion is coupled to the advancement mechanism by a rigid extension.

7. The system of claim 6, wherein the contact portion is formed as a ring that surrounds the flexible catheter.

8. The system of claim 6, wherein the contact portion has a flat surface which is flexible.

9. The system of claim 8, wherein the contact portion is formed as a tubular cage that surrounds the flexible catheter.

10. The system of claim 4, wherein the distal end of the hub body includes an o-ring to reduce ingress of blood into the hub body.

11. A method for securing an intravenous cannula in a selected position, the method comprising:
   inserting a distal portion of an intravenous cannula into a skin penetration point of a skin surface;
   advancing the intravenous cannula until a distal end enters a target body lumen and at least one subcutaneous anchor is positioned in a subcutaneous region under the skin surface;
   engaging an external anchor by applying a first force to a tab of the external anchor in a first direction parallel to a longitudinal axis of the intravenous cannula and toward the skin surface, to secure the intravenous cannula in a position above and adjacent to the skin surface;
   performing a medical procedure using the intravenous cannula;
   after the medical procedure is performed, disengaging the external anchor by applying a second force to the tab of the external anchor in a second direction parallel to a longitudinal axis of the intravenous cannula and away from the skin surface; and
   removing the intravenous cannula through the skin penetration point.

12. The method of claim 11, further comprising:

inserting a needle portion of an inserter tool through the skin penetration point and into a targeted vessel, wherein the intravenous cannula is removably coupled to the inserter tool such that a flexible catheter of the intravenous cannula is advanced through the skin penetration point and into the targeted vessel while the at least one subcutaneous anchor integrally formed as a unitary structure with an outer wall of the flexible catheter is positioned under a skin layer;

engaging the external anchor with a surface of the skin layer, wherein the external anchor is movably positioned along the flexible catheter of the intravenous cannula to a position adjacent the surface of the skin layer, and wherein the external anchor has a contact surface which is configured to be positioned in contact with the surface of the skin layer;

removing the inserter tool from the intravenous cannula such that the needle portion of the inserter tool is slidably withdrawn from a lumen of the flexible catheter while a distal opening of the flexible catheter remains in the targeted vessel to provide fluid communication with the targeted vessel, the external anchor remains in contact with the surface of the skin layer, and the at least one subcutaneous anchor remains under the skin layer;

threadably engaging an external fluid line to a proximal connector hub of the intravenous cannula while the flexible catheter remains in the targeted vessel, the external anchor remains in contact with the surface of the skin layer, and the at least one subcutaneous anchor remains under the skin layer, wherein the external anchor is positioned between a distal tip of the flexible catheter and the proximal connector hub, and wherein the at least one subcutaneous anchor is positioned distal of the external anchor toward the distal tip of the flexible catheter; and infusing a fluid from the proximal connector hub through the lumen of the flexible catheter and into the targeted vessel.

* * * * *